United States Patent [19]
Frueh et al.

[11] Patent Number: 6,033,671
[45] Date of Patent: *Mar. 7, 2000

[54] IDENTIFICATION OF HUMAN CYTOMEGALOVIRUS GENES INVOLVED IN DOWN-REGULATION OF MHC CLASS I HEAVY CHAIN EXPRESSION

[75] Inventors: Klaus Frueh, Encinitas; Young Yang, San Diego, both of Calif.; Kwangseog Ahn, Seoul, Rep. of Korea

[73] Assignee: Ortho McNeil Pharmaceutical, Inc., Raritan, N.J.

[*] Notice: This patent issued on a continued prosecution application filed under 37 CFR 1.53(d), and is subject to the twenty year patent term provisions of 35 U.S.C. 154(a)(2).

[21] Appl. No.: 08/903,805

[22] Filed: Jul. 31, 1997

Related U.S. Application Data

[60] Provisional application No. 60/022,847, Jul. 31, 1996, and provisional application No. 60/046,213, May 12, 1997.

[51] Int. Cl.[7] .......................... A61K 39/245; C12N 7/00; C12N 7/04; C12N 15/00
[52] U.S. Cl. ...................... 424/205.1; 424/230.1; 435/235.1; 435/236; 435/455
[58] Field of Search .............................. 435/173.3, 235.1, 435/320.1, 236, 455; 424/230.1, 205.1, 93.2

[56] References Cited

U.S. PATENT DOCUMENTS 5,843,458 12/1998 Jones ..................................... 424/230.1
5,843,637 12/1998 Jones et al. ................................. 435/5

FOREIGN PATENT DOCUMENTS 9604383 2/1996 WIPO ............................ C12N 15/38

OTHER PUBLICATIONS

Jones et al, J. Virology 66:2541–2546, 1992.
Greaves et al, J. Gen. Virology 76:2151–2160, 1995.
Colberg–Poley et al, J. Virology 66:95–105, 1992.
Britt, Trends in Microbiology, vol. 4(1), p. 34–37, 1996.
Kollert–Jones, et a (1991) J of Virology, vol. 65(10) p. 5184–5189.

*Primary Examiner*—Mary E. Mosher
*Attorney, Agent, or Firm*—John W. Wallen, III

[57] ABSTRACT

The human cytomegalovirus (HCMV) genomic US region encodes a family of homologous genes essential for the inhibition of major histocompatiblity complex (MHC) class I mediated antigen presentation observed during viral infection. Here we show that US3 and US6 encode ER-resident glycoproteins that prevent intracellular transport of NMC class I molecules by different mechanisms. US3 retains stable MHC class I heterodimers in the ER which are loaded with peptides while retained in the ER. US6 prevents MHC class I assembly with β2 microglobulin which results in free heavy chains leaving the ER. These genes have the potential to prevent unwanted immunological reactivities triggered by MHC class I molecules.

5 Claims, 13 Drawing Sheets

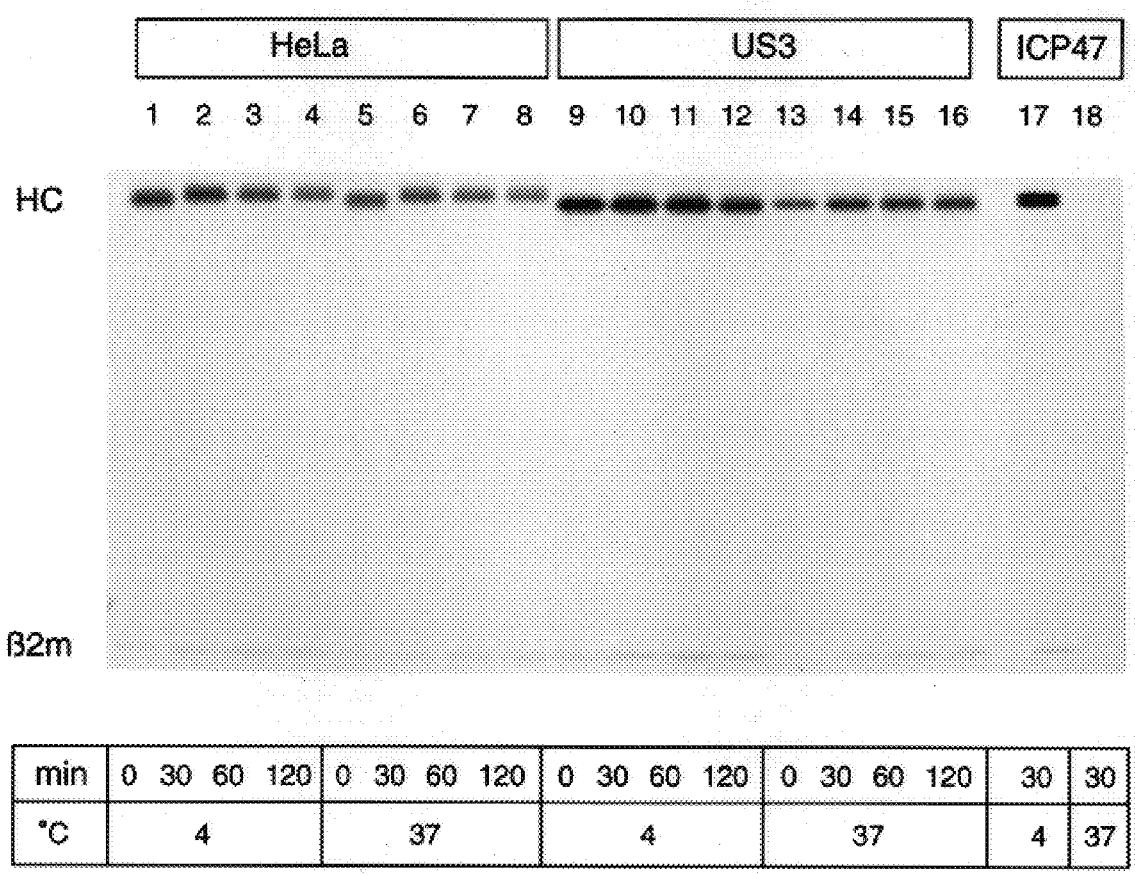

αUS6 costaining

αCalnexin

6,033,671

IDENTIFICATION OF HUMAN CYTOMEGALOVIRUS GENES INVOLVED IN DOWN-REGULATION OF MHC CLASS I HEAVY CHAIN EXPRESSION

This application claims the benefit of U.S. provisional application No. 60/022,847, filed Jul. 31, 1996, and U.S. provisional application No. 60/046,213, filed May 12, 1997.

FIELD OF THE INVENTION

The present invention relates to recombinant human cytomegalovirus (HCMV) genes whose encoded proteins down-regulate expression of cellular MHC class I heavy chains.

BACKGROUND OF THE INVENTION

Human cytomegalovirus (HCMV) is a betaherpesvirus which causes clinically serious disease in immunocompromised and immunosuppressed adults, as well as in some infants infected in utero or perinatally (Alford, C. A., and W. J. Britt. 1990. Cytomegalovirus, p. 1981–2010. In D. M. Knipe and B. N. Fields (ed.), Virology, 2nd ed. Raven press, New York). In human cytomegalovirus (HCMV)-infected cells, expression of the cellular major histocompatibility complex (MHC) class I heavy chains is down-regulated. The 230-kb dsDNA genome of HCMV was sequenced (Chee, M. S., A. T. Bankier, S. Beck, R. Bohni, C. M. Brown, R. Cerny, T. Horsnell, C. A. Hutchinson, T. Kouzarides, J. A. Martignetti, E. Preddie, S. C. Satchwell, P. Tomlinson, K. Weston, and B. G. Barrell. 1990. Analysis of the protein-coding content of the sequence of human cytomegalovirus strain AD 1 69. Curr. Top. Microbiol. Immunol. 154:125–169) and has at least 200 open reading frames (ORFs). The functions of most of these 200 genes is unknown. The function of some HCMV proteins are known or predicted due to their homology with other viral (especially herpes simplex virus) and cellular proteins. However, for the majority of the HCMV ORFS, the functions of the proteins they encode is unknown.

Several investigators have shown that infection by HCMV results in the down-regulation of cellular MHC class I heavy chains (Browne, H., M. Churcher, and T. Minson. 1992. Construction and characterization of a human cytomegalovirus mutant with the UL18 (class I homolog) gene deleted. J. Virol. 66:6784–6787; Beersma, M. F. C., M. J. E. Bijlmakers, and H. L. Ploegh. 1993. Human cytomegalovirus down-regulates HLA class I expression by reducing the stability of class I H chains. J. Immunol. 151:4455–4464; Yamashita, Y., K. Shimokata, S- Mizuno, H. Yamaguchi, and Y. Nishiyama. 1993. Down-regulation of the surface expression of class I MHC antigens by human cytomegalovirus. Virology 193:727–736). Down-regulation is defined as reduction in either synthesis, stability or surface expression of MHC class I heavy chains. Such a phenomenon has been reported for some other DNA viruses, including adenovirus, murine cytomegalovirus, and herpes simplex virus (Anderson, M., S. Paabo, T. Nilsson, and P. A. Peterson. 1985. Impaired intracellular transport of class I MHC antigens as a possible means for adenoviruses to evade immune surveillance. Cell 43:215–222; Burgert and Kvist, 1985, Cell, 41:987–997; del Val, M., K. Munch, M. Reddehasse, and U. Koszinowski. 1989. Presentation of CMV immediate-early antigen to cytotoxic T lymphocytes is selectively prevented by viral genes expressed in the early phase. Cell 58:305–315; Campbell, A. E., J. S. Slater, V. J. Cavanaugh, and R. M. Stenberg. 1992. An early event in murine cytomegalovirus replication inhibits presentation of cellular antigens to cytotoxic T lymphocytes. J. Virol. 66:3011–3017; Campbell, A. E., J. S. Slater. 1994. Down-regulation of major histocompatibiiity complex class I synthesis by murine cytomegalovirus early gene expression. J. Virol. 68:1805–1811; York, I. A., C. Roop, D. W. Andrews, S. R. Riddell, F. L. Graham, and D. C. Johnson. 1994. A cytosolic herpes simplex virus protein inhibits antigen presentation to CD8+ T lymphocytes. Cell 77:525–535). In the adenovirus and herpes simplex virus systems, the product of a viral gene which is dispensable for replication in vitro is sufficient to cause down-regulation of MHC class I heavy chains (Anderson, M., S. Paabo, T. Nilsson, and P. A. Peterson. 1985. Impaired intracellular transport of class I MHC antigens as a possible means for adenoviruses to evade immune surveillance. Cell 43:215–222; Burgert and Kvist, 1985, supra). The gene(s) involved in class I heavy chain down-regulation by murine cytomegalovirus have not yet been identified.

HCMV causes benign but persistent infections in immunocompetent individuals implying a balance between immune control of and immune escape by the virus (Rinaldo, C. R. (1990) Annu. Rev. Med. 41, 331–338). Cytotoxic T cells play a major role in the immune defense against most viruses, since infected cells can be lysed upon engagement of T-cell receptors with MHC class I molecules presenting virus derived peptides (Townsend, A. & Bodmer, H. (1989) Ann. Rev. Iiiiitiui ol. 7, 601–624). However, HCMV infection prevents T cells from recognizing viral or self antigens if they are synthesized within the cell, but not if the specific epitope is given as a peptide (Hengel, H., Esslin-er, C., Pool, J., Goulmy, E. & Koszlnowski, U. H. (1995) J.GenVirol 76, 2987–2997), consistent with HCMV interference with MHC class I assembly and a peptide transport. In non-infected cells, newly synthesized MHC class I heavy chains (HC) associate with β2-microglobulin (β2m) in the endoplasmic reticulum. Subsequently, heterodimers associate with TAP, an ATP-driven peptide transporter, and acquire 8–10 amino-acid long peptides imported from the cytosol (Heemels, M.-T. & Ploegh, H. (1995) Ann. Rev. Biocliem. 64, 463–491). This trimeric complex is then transported to the cell surface provided peptides are bound with sufficient affinity. By contrast, HCs are selectively degraded immediately after synthesis in HCMV-Infected cells (Warren, A. P., Ducroq, D. H., Lehner, P. J. & Borysiewicz, L. K. (1994) J Virol 68, 1822–2829; Yamashita, Y., Shimokata, K., Saga, S., Mizuno, S., Tsurumi, T. & Nishiyama, Y. (1994) J Virol 68, 7933–7943; Beersma, M. F. C., Bijlmakers, M. J. E. & Ploegh, H. (1993) J Iinm tiol. 151, 4455–4464). Deletion analysis has revealed that at least two loci within the growth-dispensable US-region of the HCMV genome mediate such degradation independently (Jones, T. R., Hanson, L. K., Sun, L., Slater, J. S., Stenberg, R. M. & Campbell, A. E. (1995) Journal of Virology 69, 4830–41). One of the responsible genes was identified as US 11, since US11 transfectants faithfully reproduced viral HC degradation. Interestingly, HCs appear to be exported into the cytosol for degradation in US11 transfectants (Wiertz, E. J. H. J., Jones, T. R., Sun, L., Bogyo, M., Geuze, H. J. & Ploegh, H. L. (1996) Cell 84, 769–779).

SUMMARY OF THE INVENTION

The present invention provides a method of controlling downregulation of major histocompatibility complex (MHC) class I expression in a cytomegalovirus infected cell which utilizes the recombinant US3 and/or US6 genes or their protein products from human cytomegalovirus.

The present invention also provides a vaccine which utilizes the recombinant mutant human cytomegalovirus genes or their protein products, as well as a method of immunizing an individual against cytomegalovirus employing the recombinant mutant human cylamegalovirus. A live attenuated HCMV vaccine open reading frame US3 and/or US6 will elicit a better immune response than one containing this gene region, based on the lack of class I down-regulation by the former. Therefore a virus lacking this region is a superior immunogen.

The present invention also provides a method of preventing or reducing susceptibility to acute cytomegalovirus in an individual by administering an immunogenic amount of the gene, gene products, and/or the recombinant mutant human cytomegalovirus.

The present invention also provides a gene therapy vector in which the open reading frame US3 and/or US6 of the HCMV gene involved in the MHC class I heavy chain down-regulation can be incorporated into adenovirus vectors or similar virus based gene therapy vectors to minimize the immune response. This will allow the use of the recombinant adenovirus or similar virus based gene therapy vectors to be used in gene therapy.

DETAILED DESCRIPTION OF THE INVENTION

Figure 1:
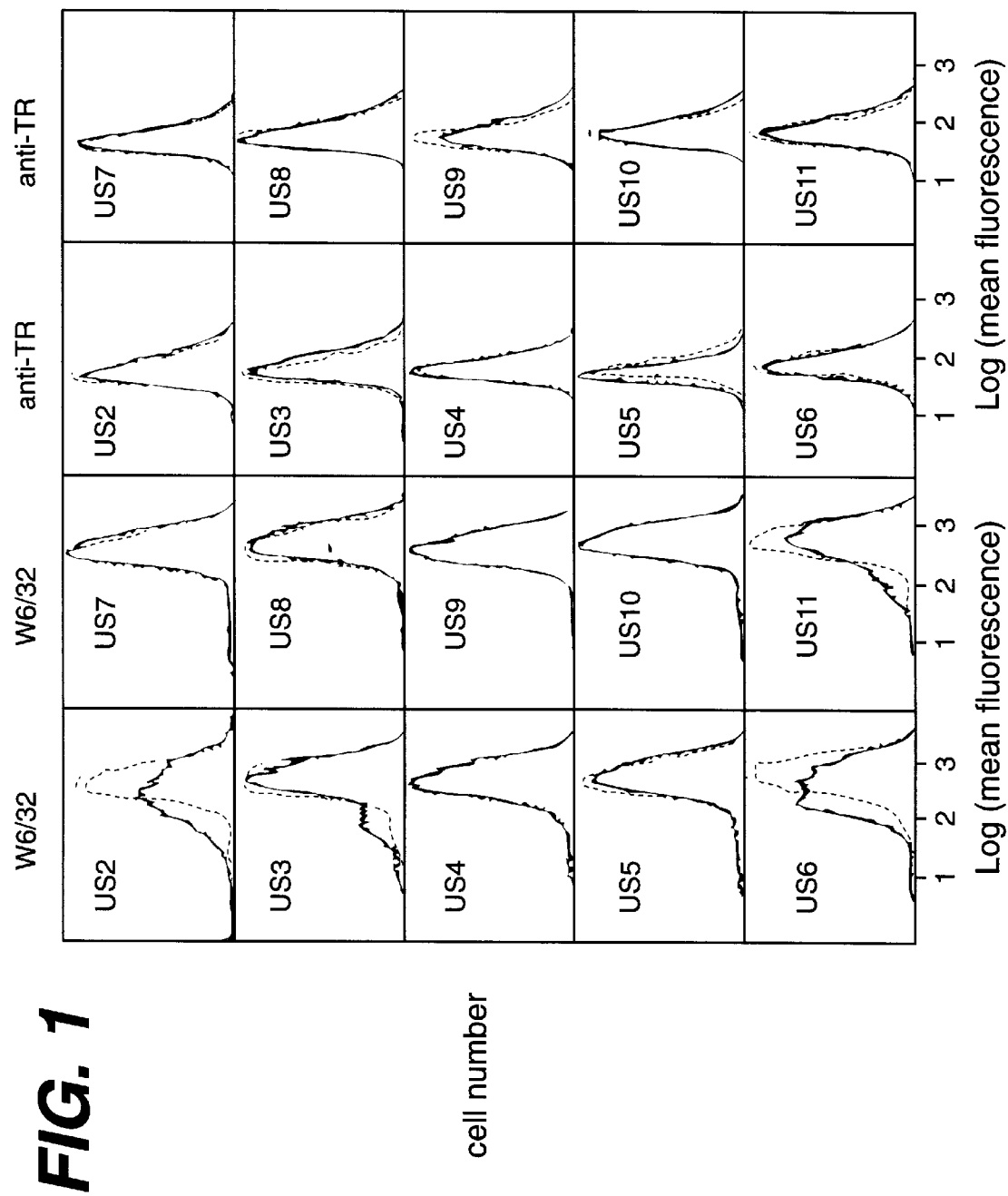
FIG. 1: Four US genes prevent MHC class I surface expression independently. Surface expression of either W6/32 reactive MHC class I heterodimers or transferrin was analysed by FACS 72 hours after transfection with the indicated US genes. Stipled lines are from non-induced transfections (+tetracycline). Solid lines are from tranfections induced for 48 hours.

The subregion of the HCMV genome which contains ORFs US2-US5 comprises bases 193119–195607. It has been proposed that US2 and US3 encode membrane glycoproteins (Chee, M. S., A. T. Bankier, S. Beck, R. Bohni, C. M. Brown, R. Cerny, T. Horsnell, C. A. Hutchinson, T. Kouzarides, J. A. Martignetti, E. Preddie, S. C. Satchwell, P. Tomlinson, K. Weston, and B. G. Barrell. 1990. Analysis of the protein-coding content of the sequence of human cytomegalovirus strain AD 1 69. Curr. Top. Microbiol. Immunol. 154:125–169). US3 is a differentially spliced gene which is expressed throughout the viral replicative cycle and encodes a protein with transcriptional transactivating activity (Tenney, D. J., and A. M. Colberg-Poley. 1991. Human cytomegalovirus UL3638 and US3 immediate-early genes: temporally regulated expression of nuclear, cytoplasmic, and polysome-associated transcripts during infection. J. Virol. 65:6724–6734; Colberg-Poley, A. M., L. D. Santomenna, P. P. Harlow, P. A. Benfield, and D. J. Tenney. 1992. Human cytomegalovirus US3 and UL36-38 immediate-early proteins regulate gene expression. J. Virol. 66:95–105; Tenney, D. J., L. D. Santomenna, K. B. Goudie, and A. M. Colberg-Poley. 1993. The human cytomegalovirus US3 immediate-early protein lacking the putative transmembrane domain regulates gene expression. Nucl. Acids Res. 21:29312937; Weston, K. 1988. An enhancer element in the short unique region of human cytomegalovirus regulates the production of a group of abundant immediate early transcripts. Virology 162:406–416). Several smaller ORFs are also present in this subregion (between the ORFs US3 and US5), but their expression characteristics or functions have not been reported. Gretch, D. R., and M. F. Stinski 1990 (Transcription of the human cytomegalovirus glycoprotein gene family in the short unique component of the viral genome. Virology 174:522–532) reported that there is a 1.0-kb early mRNA transcribed from this region of the HCMV genome, but it was not finely mapped. It has been previously shown that expression of the US2 gene is sufficient for MHC class I down-regulation within this locus (US2-US5).

Another HCMV subregion, which is also sufficient for MHC class I heavy chain reduction, contains the US10 and US11 genes, at bases 199083–200360. However, for the US10 gene product, US10 expression is not sufficient for down-regulation of heavy chain expression. It is demonstrated herein that US3 and US6 expression is sufficient to cause MHC class I heavy chain down-regulation in stably-transfected uninfected cells in the absence of other HCMV proteins.

RNA and protein expression from US11 begins early and proceeds throughout the course of infection (Jones, T. R., and Muzithras, V. P. 1991. Fine mapping of transcripts expressed from the US6 gene family of human cytomegalovirus strain AD 1 69. J. Virol. 65:2024–2036). US11 encodes a glycoprotein of 32-kDa (gpUS11) which has N-linked sugar residues that are endoglycosidase H sensitive. Immunofluorescence experiments show that gpUS11 is not present on the cell surface, but is detected in the cytoplasm of HCMV-infected cells. Thus, gpUS11 is retained in the endoplasmic reticulum or cis golgi. The characteristics of HCMV gpUS11 are similar to the 25-kDa glycoprotein (E3-19K) encoded from the E3 region of adenovirus type 2. Ad E3-1 9K is nonessential for viral replication. It has been shown to contain endoglycosidase H-sensitive N-linked sugar residues, be retained in the endoplasmic reticulum, and bind MHC class I heavy chains, thereby preventing their transport to the cell surface 9 (Anderson, M., S. Paabo, T. Nilsson, and P. A. Peterson. 1985. Impaired intracellular transport of class I MHC antigens as a possible means for adenoviruses to evade immune surveillance. Cell 43:215–222; Burgert, H. G., and S. Kvist. 1985. An adenovirus type 2 glycoprotein blocks cell surface expression of human histocompatibility class I antigens. Cell 41:987–997). In contrast to Ad E3-19K, a direct association between gpUS11 and class I heavy chains (i.e., by coimmunoprecipitation) was not detected.

The identification of the US2-US11 gene region as the region of the HCMV genome required for down-regulation of MHC class I heavy chains is significant in several respects. As mentioned above, expression from this region of the genome throughout the course of infection acts to interfere with an effective cell mediated immune response. Surface expression of MHC class I molecules is required for antigen presentation to activate and expand cytotoxic T lymphocyte (CTL) precursors populations (Schwartz, R. H. 1985. T lymphocyte recognition of antigen in association with gene products of the major histocompatibility complex. Ann. Rev. Immunol. 3:237–261). In addition, they are further required for target recognition by the activated CTLs (Zinkernagel, R. M., and P. C. Doherty. 1980. MHC restricted cytotoxic T cells: studies on the biological role of polymorphic major transplantation antigens determining T cell restriction specificity. Adv. Immunol. 27:51–177). In MCMV, CTLs against the major immediate-early protein are protective against lethal infection by this virus. However, in HCMV infected individuals, the frequency of CTLs against the analogous HCMV immediate-early protein, 1E1, are reported to be extremely rare (Gilbert, M. J., S. R. Riddell, C-R. Li, and P. D. Greenberg. 1993. Selective interference with class I major histocompatibility complex presentation of the major immediate-early protein following infection with human cytomegalovirus. J. Virol. 67:3461–3469). Recent studies have shown that IE peptides are more efficiently presented by interferon γ-treated HCMV-infected cells, than by untreated infected cells (Gilbert, M. J., S. R. Riddell, C-R. Li, and P. D. Greenberg. 1993. Selective interference with class I major histocompatibility complex presentation of the major immediate-early protein following infection with human cytomegalovirus. J. Virol. 67:3461–3469). Interferon γ causes increased surface expression of MHC class I proteins. Thus, increasing the expression of class I heavy chains in HCMV infected cells may be important in the efficient generation of IE-specific CTLS, or CTLs against other important HCMV antigens. A HCMV mutant deleted of the US3 and/or US6 gene region would have this effect since the class I heavy chains are not down-regulated when cells are infected with this mutant. Therefore, a deletion of this region of the viral genome is important in the development of a live HCMV vaccine to induce an effective anti-HCMV immune response.

The elucidation of the US3 and US6 gene products as being sufficient for class I down-regulation is significant for several reasons based on the fact that class I proteins mediate the activation of, and recognition of target cells by, cytotoxic T lymphocytes, the primary player in the cellular immune response. US3 and US6, as genes or, perhaps, as proteins, may be incorporated in clinical treatment strategies when expression of cellular MHC class I is undesirable: gene therapy vectors (e.g., adenovirus vectors) and to reduce allograft rejection. US3 and US6 can be used as tools to identify other cellular proteins which may interact with class I heavy chains and thereby effect class I heavy chain protein stability, processing, and transport to the cell surface. In an HCMV vaccine strategy using a live virus, removal of US3, or US6, or both may yield a virus which is a better immunogen than a virus which contains these genes.

A pharmaceutical composition may be prepared containing a recombinant HCMV mutant in which the region of the HCMV genome capable of down-regulating MHC Class I expression in infected cells has been deleted. The deleted region of the HCMV genome is preferably open reading frame US3, US6, or both. A stabilizer or other appropriate vehicle may be utilized in the pharmaceutical composition.

As discussed earlier, the recombinant HCMV mutant of the present invention from which a region of the HCMV genome capable of down-regulating MHC class I expression has been deleted, may be used in a vaccine for the prevention of cytomegalovirus infections. The deleted region of the HCMV genome is preferably open reading frame US3, US6, or both. The vaccine comprises an effective amount of the recombinant HCMV mutant in a pharmaceutically acceptable vehicle. An adjuvant may be optionally added to the vaccine.

A method of immunizing an individual against cytomegalovirus may be carried out by administering to the individual an immunogenic amount of a recombinant HCMV mutant which is devoid of the gene sequence capable of down-regulating MHC class I expression. The gene sequence which has been deleted is preferably the region containing open reading frame US3, US6, or both.

A method of preventing or reducing susceptibility in an individual to acute cytomegalovirus may be carried out by administering to the individual an immunogenic amount of a recombinant HCMV mutant which is devoid of the gene sequence capable of down-regulating MHC class I expression. The gene sequence which has been deleted is preferably the region containing open reading frame US3, US6, or both.

Down-regulation of MHC class I expression in a cytomegalovirus infected cell may be controlled by a method having the steps of identifying a gene sequence capable of down-regulating the major histocompatibility complex and deleting the identified gene sequence from the cytomegalovirus genome.

As discussed earlier, the gene sequence involved in the MHC class I heavy chain down-regulation can be incorporated into adenovirus vectors or similar virus-based gene therapy vectors to minimize the immune response and allow the use of the vectors in gene therapy. One virus-based gene therapy vector comprises the gene sequence of the open reading frame of US3. Another virus based gene therapy vector comprises the gene sequence of the open reading frame of US6. Another virus-based gene therapy vector comprises the gene sequences of US3 and US6, respectively.

In order to identify other immunosupressive genes in the US region of HCMV we have cloned US2 trough US11 and expressed them in HeLa cells. Here we demonstrate that four genes, US2, US3, US6 and US11 are indenpendently able to prevent surface expression of MHC class I molecules. We further show that US3 retains MHC class I molecules in the ER, whereas US6 prevents the association of β2m with the heavy chain.

The following Examples are provided to illustrate the present invention without, however, limiting the present invention thereto.

EXAMPLE 1

DNA Constructs

Genes coding for US2, US3, US4, US5, US6, US7, US8, US9, US10 and US11 were amplified by polymerase chain reaction using HCMV genomic cosmid pCM 1052 as template (Fleckenstein, B., Muller, 1. & Collins, J. (1982) *Gene* 18, 39–46). All 5'-end primers contained the SacII restriction site CCGCGG followed by the sequence CCACCATG corresponding to a consensus initiation signal (Kozak, M. (1984) *Nucleic Acid Res.* 12, 857–872). The start codon represented the first three nrucleotides of the respective open reading frames for all genes except for US4 which does not contain a start codon by itself. The following 20–30 nucleotides hybridizing to the US-DNA were synthesized according to the HCMV sequence (Chee, M. S., Bankier, A. T., Beck, S., Bohni, R., Brown, C. M., Cerny, R., Horsnell, T., Hutchinson 111, C. A., Kouzarides, T., Marti-netti, J. A., Preddle, E., Satchwell, S. C., Tomlinson, P., Weston, K. M. & Barrell, B. G. (1990) Curr. Top. Microhiol. Immunol. 154, 125–169) for all US-sequences except for US7 where a silent mutation was introduced by replacing the G at position 6 of the coding region with a T in order to remove a Bam HI recognition site. All 3'-primers contained the last 20 to 30 nucleotides of the codon sequences followed by a stop codon and a Bam HI restriction site. Amplified DNA fragments were inserted as Sac II/Bam HI into the tetracycline inducible expression vector pUHGIO-3 (Gossen, M. and Bujard, H. (1992) Proc.Natl.Acad.Sci. USA, 89,5547–5551).

Transfections and Stable Cell Lines

HeLa cells containing the tetracycline regulatable transactivator (Gossen, supra) were transfected by the calcium phosphate method. To establish stable cell lines, pUHG. 10-3.US constructs were cotransfected with a plasmid conferring Ouabain resistance (Yang, Y., Frueh, K., Ahn, K. & Peterson, P. A. (1995) J. Biol. Chem. 270, 27687–27694). Stable clones were selected in the presence of Ouabain (1 $\mu$M) for 24 hours each week. Single cell colonies were screened by FACS analysis for tetracycline inducible reduction of MHC class I surface expression and by immunoprecipitation for expression of the respective US-genes.

EXAMPLE 2

Antibodies

Rabbit antisera specific for US3, US6 and US11 were raised against the following synthetic peptides indicated by the position of the first amino-acid in the respective coding sequence: US3-N, 16-35; US3-C, 78-97; US 6-N, US6-C, US11-N, 16-36; US11-C, 100-118.

MHC class I specific antisera K455 and K355 were raised against purified human class I heterodimers or human $\beta$2-microglobulin, respectively (Andersson, M., Paabo, S., Nilsson, T. & Peterson, P. A. (1985) Cell 43, 215–222). K455 recognizes HC and $\beta$2m in both assembled and non assembled forms. K355 and monoclonal antibody BBM.1 (Brodsky, F. M., Parham, P., Barnstable, C. J., Crumpton, M. J. & Bodmer, W.F. (1979) Immuiiol. Rev. 47, 3) recognize both free and complexed $\beta$2m. Monoclonal antibody W6/32 recognizes only the complex of HC and $\beta$2m (Brodsky, supra). Monolconal antibody HCIO recognizes only free heavy chains (Stam, N. J., Spits, H. & Ploegh, H. L. (1986) J Ittinuizol. 137, 2299–2306) For detection of metabolically labeled transferrin receptor we used mab H68 (White, S., Miller, K., Hopkins, C. & Trowbridge, 1. S. (1992) Bioch. Biophys.Acta 1136, 28–34). Surface transferrin receptor was detected by using a FITClabeled commercial antibody (Pharmingen).

Metabolic Labeling and Immunoprecipitation

HeLa cell transfectants were methionine starved for 30 minutes in methionine deficient medium prior to pulse labeling for 15 or 30 minutes using 0.5 mCi $^{35}$S-Methionine (TranS-label, Amersham). The label was chased for various times with DMEM containing 10% FCS. After one wash with cold PBS, cells were lysed using 1% NP40 in PBS or 1% digitonin in PBS for 30 minutes at 4° C. Immunoprecipitations and SDS-PAGE were carried out as described (Yang, Y., Waters, J. B., FrOh, K. & Peterson, P. A. (1992) Proc Natl Acad Sci USA 89, 4928–32). For EndoH treatment, immunoprecipitates were digested with 3 mU EndoH (Boehringer Mannheim) for 16 hours at 37° C. in 50 mM NaOAc pH 5.6, 0.3% SDS, 150 mM 2-mercaptoethanol.

FACS Analysis $10^5$ HeLa cells were stained with W6/32 (1:100) or FITC anti-transferrin receptor (1:10) for 1 hour followed by three washes in PBS, 1% BSA. Bound W6/32 was visualized with goat-anti-rabbit IgG fluorescein conjugate (Cappel). Negative control was only goat-anti-rabbit IcG fluorescein conjugate.

Viral Infections

HCMV wild type, strain AD 169 was obtained from the American Type Culture Collection and HCMV mutants were constructed as previously described (Jones et al., 1995). Human foreskin fibroblast (HFF) cells were cultured as adherent monolayers in Dulbecco's modified Eagle's medium (DMEM) supplemented with 10% fetal calf serum, penicillin, streptomycin and 2 mM glutamine. HFF cell monolayers ($10^7$ cells) were infected with HCMV wild type or HCMV mutants at a m.o.i. of 5 in 10 ml of Dulbecco's modified Eagle's medium (DMEM) supplemented with 10% fetal calf serum, penicillin, streptomycin and 2 mM glutamine. Two hours postinfection medium was removed and 50 ml of the same medium was added. Cells were cultured for 3 days. Infection was assessed by the cytopathic effect observed in most of the cells 72 hours postinfection.

Transfections and Stable Cell Lines

HeLa cells containing the tetracycline regulatable transactivator (HtTa cells) (Gossen and Bujard, 1992) were transfected with 24 $\mu$g plasmid DNA by $Ca^{2+}/PO_4^-$-precipitation as described in (Jackson et al., 1990). For transient experiments, $10^6$ HtTa cells were incubated with the transfection solution for 16 h prior to washing three times with PBS to remove tetracycline. Transfectants were analyzed 48 h hours after induction. To establish a stable cell line expressing US6, pUHG10.3-US6 was cotransfected with a plasmid conferring Ouabain resistance (Yang et al., 1995). Stable clones were selected by adding Ouabain (1 $\mu$M) for 24 h each week. Single cell colonies were screened by cytofluorometry for tetracycline inducible reduction of MHC class I surface expression. Stable transfectants expressing US3, US11 or ICP47 have been described previously (Ahn et al., 1996a; Früh et al., 1995).

Metabolic Labeling and Immunoprecipitation

For pulse/chase experiments, $10^6$ cells were methionine starved for 30 min prior to pulse labeling for the indicated times using 0.5 mCi$^{35}$S-Methionine (TranS-label, Amersham). The label was chased for various times with DMEM containing 10% FCS. For optimal labeling of TAP, cells were labeled for 16 h with 0.4 mCi in DMEM containing 1% FCS dialyzed using a 12 KD cutoff membrane. After labeling, cells were washed once with cold PBS and lysed using 1% NP40 (Sigma) in PBS or 1% digitonin (Calbiochem) in PBS for 30 min at 4° C. Immunoprecipitations and SDS-gels were carried out as described (Yang et al., 1992). For EndoH treatment, immunoprecipitates were digested with 3 mU EndoH (Boehringer Mannheim) for 16 h at 37° C. in 50 mM NaOAc pH 5.6, 0.3% SDS, 150 mM 2-mercaptoethanol.

Immunofluorescence and Cytofluorometry

For immunofluorescence transiently transfected HeLa cells were fixed in 4% paraformaldehyde and permeabilized with 0.1% Triton X-100 followed by incubation with antisera US6-N and mab AF8 for 1 h. Bound rabbit or mouse antibody was visualized with goat-anti-rabbit IgG fluorescein or goat-anti-mouse rhodamin conjugate, respectively (Cappel). Cytofluorometric analysis was performed using goat-anti-rabbit IgG FITC to detect W6/32 specific for human MHC class I heterodimers (Parham, 1983).

Peptide Transport Assays

HCMV infected HFF cell monolayers were detached with trypsin/EDTA, washed twice with transport buffer (130 mM KCl, 10 mM NaCl, 1 mM $CaCl_2$, 2 mM EGTA, 2 mM $MgCl_2$, 5 mM Hepes, pH 7.3 with KOH) at 4° C. and then permeabilized ($10^7$ cells/ml) in transport buffer containing 4 U/ml of Streptolysin O (SLO) for 20 min at 37° C. Permeabilization was assessed by trypan blue exclusion. Permeabilized cells ($10^6$ cells/sample in eppendorf tubes) were incubated for 10 min at 37° C. with 10 ml of a radioiodinated peptide library (Heemels et al., 1993) and 10 ml of ATP generating system (50 mM ATP, 250 mM UTP, 2.5 mM creatine phosphate and 8U creatine phosphokinase) in a total volume of 100 ml at 37° C. When indicated, synthetic ICP47 87 mer was added to the translocation mixture in 10 ml at a final concentration of 10 mM. Peptide translocation was terminated by adding 1 ml of ice-cold stop buffer (transport buffer+10 mM EDTA, 0.02% sodium azide). Samples were centrifugated at 14.000 r.p.m., supernatant was removed and 1 ml of ice-cold lysis buffer (0.5% NP40, 5 mM $MgCl_2$, 50 mM Tris-HCl pH 7.5) added. After 20 min, nuclei were removed by centrifugation at 14.000 r.p.m. and the supernatant incubated with gentle agitation for 1 hour with 100 ml of Con A Sepharose beads at 4° C. Beads were washed three times with lysis buffer and radioactivity quantitated by g-spectrometry.

MHC Class I Heterodimers are Retained in the Endoplasmic Reticulum in US 3 Transfected HeLa Cells To test which US genes interfere with MHC class I surface expression, we cloned the PCR amplified coding region of US2 through US11 into the tetracycline-regulatable expression vector PUHG.10-3 and transiently transfected tet-transactivator-containing HeLa cells (HtTa). As expected from previous data we observed a reduction of MHC class I surface expression in US11 transfectants whereas surface expression of transferrin receptors was not affected (FIG. 1). In addition we observed similar effects for US2, US3 and US6.

Figure 2A:
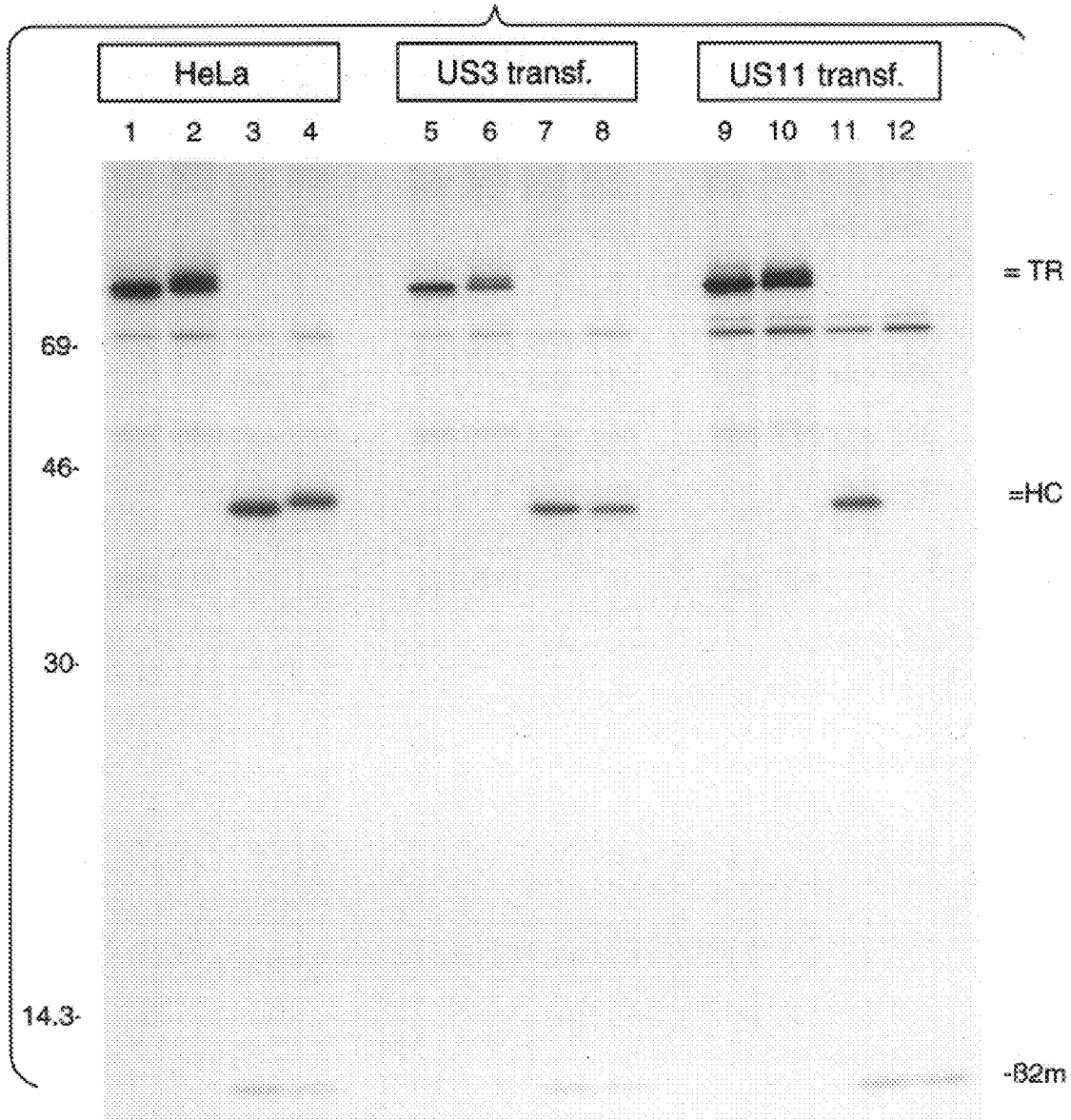
FIG. 2, Panels A and B: Intracellular transport of transferrin receptor and MHC class I in US3 and US11 transfected HeLa cells. Panel A) Stably transfected or non-transfected HeLa cells containing the tet-regulatable transactivator (Gossen, M. & Bujard, H. (1992) *Proc. Natl. Acad. USA* 89, 5547–5551) were grown for 24 hours in the absence of tetracycline to induce US3 and US11 expression and biosynthetically labeled for 15 minutes (odd numbered lanes) followed by 30 minute chase (even numbered lanes). Lysates were immunoprecipitated with antitransferrin receptor antibody (lanes 1, 2, 5, 6, 9, 10) or anti-MHC class I antiserum K455 (lanes 3, 4, 7, 8, 11, 12). The size of the molecular weight standard in kDa is indicated. Panel B) MHC class I immunoprecipitates of non-transfected or US3-transfected HeLa cells biosynthetically labeled as above were untreated (odd-numbered lanes) or treated with EndoH (even numbered lanes) prior to SDS-PAGE. (EndoHs, EndoHr indicates EndoH-sensitive or -resistant HCs, respectively). Immunoprecipitates in lanes 1, 2, 5, 6 were only pulse labeled, whereas lanes 3, 4, 7, 8 correspond to 30 minute chase. Only the part of the gel displaying the HC is shown.
Figure 2B:
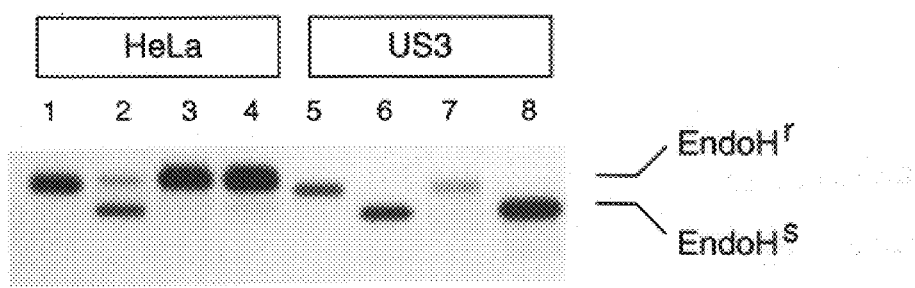

MHC class I Heterodimers are Retained in the Endoplasmic Reticulum in US3 Transfected HeLa Cells We stably transfected HeLa cells with US3 and, as control, US11 and compared the intracellular transport of transferrin receptors and MHC class I molecules in either transfectants by metabolic labeling and immunoprecipitation. Neither US3 nor US11 affected the transport of transferrin receptors to the cell surface, since the single protein species of 95 kDa observed after biosynthetically labelinc, for 15 minutes was converted into a higher molecular weight protein species corresponding to the EndoH-resistant form (Wiertz, supra) within the 30 minutes chase period. Newly synthesized MHC class I HCs also display a shift in apparent molecular weight in non-transfected HeLa cells after a 30 minute chase (FIG. 2A, lane 4) and acquire Endo H resistance indicating transport through the Golgi-compartment (FIG. 2B, lane 4). However, in US3- or US11-transfected HeLa cells, intracellular transport of MHC class I HCs was inhibited although their initial synthesis, translocation and glycosylation was not affected (FIG. 2A, compare lanes 3, 7 and 11). In US11 transfectants, HCs were degraded within 30 minutes chase whereas β2m was not affected (FIG. 2A, lane 12) consistent with previous observations (Wiertz, supra). By contrast, MHC class I molecules were not degraded during the 30 minute chase period in US3 transfected cells (FIG. 2A, lane 8) but remained in the ER as indicated by their EndoH sensitivity (FIG. 1B, lane 8). These results suggested that US3 prevented MHC class I molecules from leaving the ER by a mechanism different from US11.

US3 Associates with MHC Class I Heteromers

Figure 3:
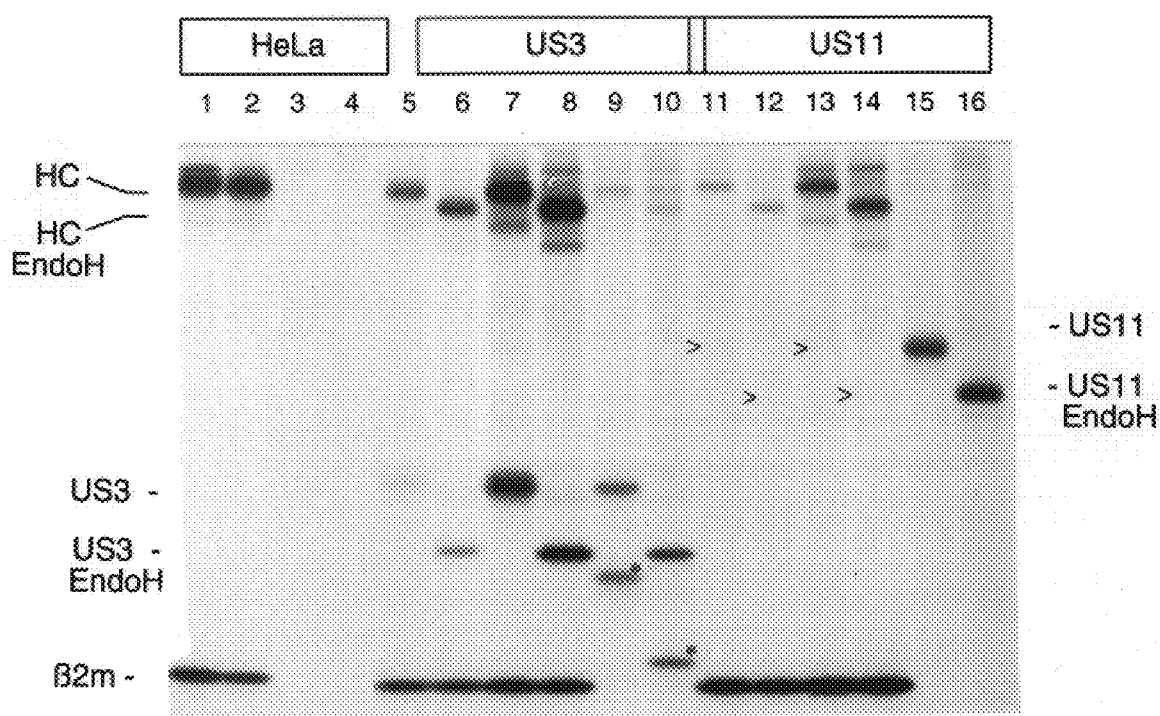
FIG. 3: US3 but not US11 coimmunoprecipitates with MHC class I The indicated cell lines were grown in the absence of tetracycline for 24 hours prior to labeling for 30 minutes and lysis in 1% digitonin. MHC class I specific antibodies used for immunoprecipitations were K355 (lanes 1, 5, 6, 11, 12) and K455 (lanes 2, 7, 8, 13, 14). Similar results were obtained using antibodies W6/32 and BBM.1. US3 and US11 were inunnunoprecipitated using anti-US3-N (lanes 3, 9, 10) and anti-US11-N (lanes 4, 15 16). Lanes 6, 8, 10, 12, 14, and 16 were treated with EndoH prior to SDS-PAGE. Lanes 1–4 are from a different gel. To the right of (>) a faint EndoH-sensitive protein is apparent which corresponds in size to US11. (*) marks a putative alternative splice product of US3. The molecular weight for glycosylated US3 and US11 was 22 kDa and 28.5 kDa, respectively, and after EndoH treatment 19 kDa and 25 kDa, respectively.

The EndoH sensitivity observed for MHC class I molecules in US3 transfected cells suggested that US3 associated with MHC class I molecules. However, no coprecipitation of US3 or US11 with MHC class I molecules was observed when cells were solubilized with NP40 (FIG. 2A, see also FIG. 4A). Therefore, we solubilized metabolically labeled US3-transfectants with the milder detergent digitonin prior to immunoprecipitation with MHC class I or US3-specific antisera (FIG. 3). Under these conditions both anti-HC and anti-β2m antisera coprecipitated a 22 to 23 kDa protein from US3 transfectants but not from HeLa cells (FIG. 3, compare lanes 1 and 2 with 5 and 7). The 22 kDa protein comigrated with a US3 detected by the US3-N antiserum (FIG. 3, lane 9, for control see lane 3). Since US3 is potentially glycosylated, we digested immunoprecipitates with EndoH prior to SDS-PAGE (FIG. 3, lanes 6, 8, 10). As observed above, the molecular weight of MHC class I HCs was reduced by approximately 3 kDa by EndoH treatment in US3 transfectants. In addition, the apparent molecular weight of the 22–23 kDa protein coprecipitated with MHC class I specific antibodies was reduced to 19 kDa. The exact same reduction in molecular weight was observed for US3 immunoprecipitated by US3-N (FIG. 3, lane 10). Together with the fact that US3 without the putative signal sequence has a predicted molecular weight of 19.9 kDa, these findings clearly identify the protein coprecipitated by MHC class I antibodies as glycosylated US3. Furthermore, the EndoH sensitivity of US3 indicates that US3 is not transported through the Golgi compartment which confirms our immunofluorescence results. In the reverse experiment, only minor amounts of MHC class I molecules were coimmunoprecipitated by US3-N (FIG. 3, lanes 9 10). This might either indicate that the majority of US3 is not bound to MHC class I in these transfected cells or that US3-N disrupts or does not recognize the complex. An additional protein of 17.5 kDa (indicated by *) was immunoprecipitated by US3-N but not by any of the anti-class I antibodies. This protein seems to be glycosylated since its molecular weight shifted to 13.5 kDa after EndoH treatment. The 13.5 kDa product might be generated by alternative splicing of US3 transcripts which has been shown to give rise to several alternative US3 RNAs in HCNW infected cells (Weston, K. (1988) *Virology* 162, 406–16) which share the 5' end allowing for translocation and glycosylation (Tenney, D. J., Santomenna, L. D., Goudie, K. B. & Colberg-Poley, A. M. (1993) *Nucleic Acids Res* 21, 2931–7). Therefore, it is possible that the 17.5 kDa glycoprotein corresponds to a form of US3 lacking the transmembrane domain. Reprecipitations of US3-N inunuprecipitates with US3-C are in agreement with this assumption. The finding that the 17.5 kDa protein is not coprecipitated by any of the anti-class I antibodies used in these experiment suggests that only the full length US3 glycoprotein associated with MHC class I molecules. The data further suggest that US3 associates in the ER with MHC class I heteromers or, alternatively, binds to free HC or β2m without preventing further assembly of the respective polypeptide chain with its partner as well as peptides.

Since an association of US11 with HC has not been demonstrated so far we used the same labeling and lysis conditions to immunoprecipitate MHC class I molecules from US11 transfected cells (FIG. 3, lanes 11–16). All HC detected in US11 cells were EndoH sensitive (FIG. 3, lanes 11, 14) as was the 29 kDa US11 protein itself which was immunoprecipitated by US11-N (FIG. 3, lanes 15, 16). The reduction of the molecular weight of US11 to 25 kDa by EndoH treatment is consistent with a predicted molecular weight of 25.3 kDa. Although a faint EndoH sensitive protein band of the size of US11 was coimmunoprecipitated by the class I-specific antisera (indicated by >) from US11 transfectants, suggested that US11 associates with MHC class I, the amount of US11 bound to the labeled MHC class I molecules was much lower than that observed for US 3. It is possible that detergent solubilization disrupts a US11 class I complex or that none of the antibodies were able to recognize such a complex. The most likely explanation however, is that US11 interacts with MHC class I molecules only very transiently followed by the rapid degradation of both free and assembled HCs.

US3 Retained MHC Class I Molecules Acquire Peptides

To identify whether US3 retains MHC class I molecules prior to or after peptide loading we monitored peptide loading by subjecting NP40 solubilized MHC class I complexes to elevated temperatures followed by immunoprecipitation with confon-nation-specific antibodies (Townsend, A., Elliot, T., Cerundolo, V., Foster, L. Barber, B. & Tse, A. (1990) *Cell* 62, 285). As control we used HeLa cells transfected with the Herpes simplex virus protein ICP47 which blocks translocation of MHC class I binding peptides into the ER (Hill, A., Jugovic, P., York, I., Rus, G., Bennink, J., Yewdell, J., Ploegh, H. & Johnson, D. (1995) *Nature* 375, 411–415; Frueh, K. et al., (1995) Nature 375, 415–418). Consequently, MHC class I molecules from ICP47 transfected cells fall apart after incubation at 37° C. for 60 minutes as monitored by inununoprecipitation with the heteromerspecific mab W6/32 (FIG. 4, lanes 17, 18). By contrast, about 85% of W6/32-reactive MHC class I molecules were thermostable in HeLa cells at all time points (FIGS. 4A, B). However, in US3 transfectants the proportion of thermostable MHC class I molecules increased during the two hour chase period as shown (FIGS. 4A, B) indicating that MHC class I molecules acquire peptides at a slower rate in US3 transfectants compared to wild-type cells. We conclude that US3 associates with MHC class I molecules prior to peptide loading and that this association slows down but does not prevent peptide loading. Since no increase in HC degradation was evident in US3 transfectants compared to HeLa cells during the two hour chase period, we further conclude that retention by US3 does not induce HC degradation as observed for US11.

US6 Prevents Assembly of HC with β12m

Figure 5:
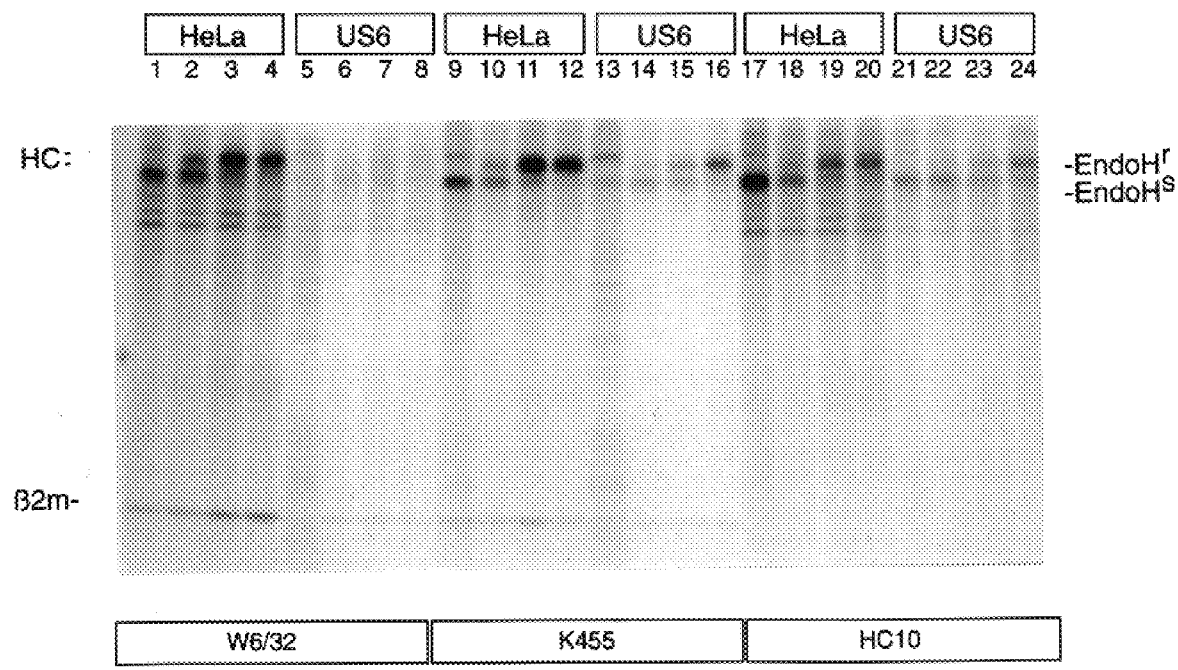
FIG. 5: MHC class I heterodimers but not free heavy chains are absent in US6 transfectants. Pulse/chase analysis of either HeLa cells or US6 transfected HeLa cells induced for 48 hours by tetracycline removal. Cells were labeled for 15 minutes and the label was chased for 0, 15, 40 and 75 minutes. Heterodimers were detected with mab W6/32, total amount of MHC class I molecules with K455 antiserum and free heavy chains with mab HC1O as indicated. Prior to SDS-PAGE all samples were treated with EndoH.

We stably transfected HeLa cells with US6 and compared the intracellular transport of MHC class I molecules to non-transfected HeLa cells by metabolic labeling and immunoprecipitation (FIG. 5). In HeLa cells, large amounts of free heavy chains can be detected immediately after the pulse (lane 17) most of which are converted to W6/32 reactive material during the chase period. By contrast, almost no W6/32 reactive heterodimer population was detected in US6 transfectants throughout the experiment, indicating that US6 affected heterodimer formation.

However, less reduction was observed in US6 transfectants for both total class I and free heavy chains. Thus US6 seems to selectively affect the formation of heterodimers, whereas it does not affect synthesis and transport of a HCl O-reactive free heavy chain population. We conclude that US6 functions different from US3, since it does not retain class I molecules. Furthermore, US6 differes from US11 in that it prevents heterodimer formation.

US6 Prevents Peptide Translocation by TAP

Figure 6:
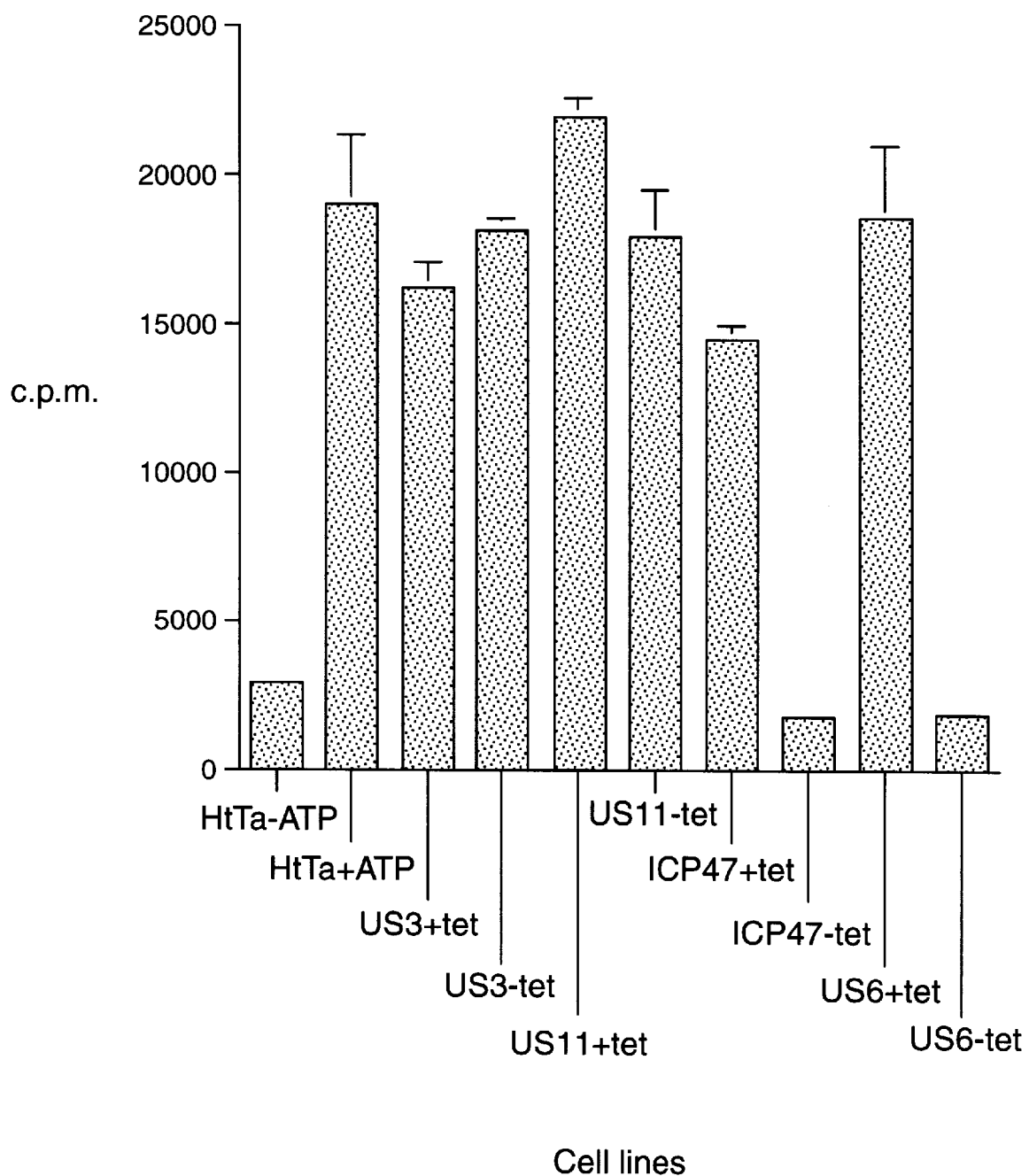
FIG. 6: Peptide translocation in US transfected HeLa cells is shown. Translocation of iodinated peptide RYNATGRL into the ER of non-transfected HtTa cells or stably transfected with US3 (Ahn et al., 1996a), US11 (Ahn et al., 1996a), ICP47 (Früh et al., 1995) or US6 was measured after tetracycline had been removed for 24 hours (-tet) to induce expression. 0.15 U Streptolysin O (Murex) was activated for 10 min at 37° C. in 100 μl transport assay buffer (Neefjes et al., 1993) containing 4 mM DTT and 10 mM fresh ATP. Transfected or untransfected HeLa cells (2×10⁶) were resuspended in this solution and after adding 2×10⁶ cpm labeled RYNATGRL cells were incubated at 37° C. for 25 min. ConA precipitation was perfomed as described (Neefjes et al., 1993). As control no ATP was added and residual ATP was removed by Apyrase in non-transfected HtTa cells prior to measuring peptide transport. Results are presented as the mean of duplicate experiments (+/− standard deviation).

Since ICP47 inhibits TAP we examined whether US6 directly affected peptide translocation. Using an established assay which monitors peptide translocation independent of MHC class I binding by ConA precipitation of peptides glycosylated upon entry in the ER (Neefjes et al., 1993) we compared TAP activity in non-transfected HtTa cells or in cells stably transfected with US3, US11, ICP47 or US6 (FIG. 6). No significant difference in the amount of glycosylated peptides was observed between non-induced or induced US3 and US11 cells (FIG. 6) or U373 cells transfected with US2. By contrast, peptide transport activity was completely inhibited in cells expressing US6 similar to ICP47 transfectants or after ATP removal. Since peptide translocation was inhibited independently of MHC class I loading, we conclude that peptide loading and impaired MHC class I transport are downstream events of TAP inhibition by US6.

US6 Inhibits TAP in HCMV Infected Cells

Figure 4B:
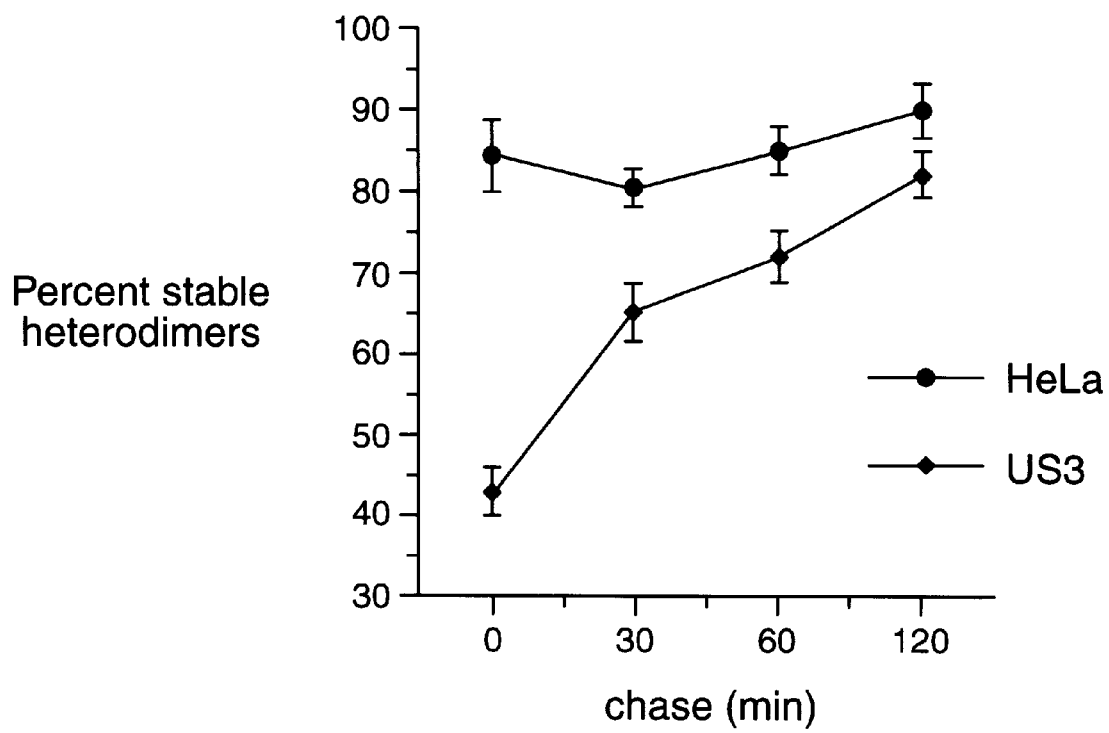
FIG. 4, Panels A and B: Thermostability of US3 retained MHC class I molecules. Panel A) Non-transfected, US3 transfected or ICP47-transfected (Friih, K., Ahn, K., Djaballah, H., Semp6, P., van Endert, P. M., Tamp6, R., Peterson, P. A. & Yang, Y. (1995) *Nature* 375, 415–418) HeLa cells were induced by tetracycline-removal for 24 hours prior to labeling for 15 minutes followed by the indicated chase times. Lysates in 1% NP40 were either kept at 40° C. or incubated for 1 hour at 37° C. prior to immunoprecipitation with W6/32. Note that MHC class I molecules in HeLa cells migrate slower after chase due to carbohydrate modifications in the Golgi (see FIG. 1). Lysates of ICP47 transfected cells contain both ER-retained and surface expressed MHC class I molecules, but both populations are unstable indicating lack of stabilizing peptides (lanes 17 and 18 are from a different gel). Panel B) the ratio of β2m coprecipitated by W6/32 after temperature challenge is shown for each time point. Data points are the mean of three experiments (± standard deviation).
Figure 7A:
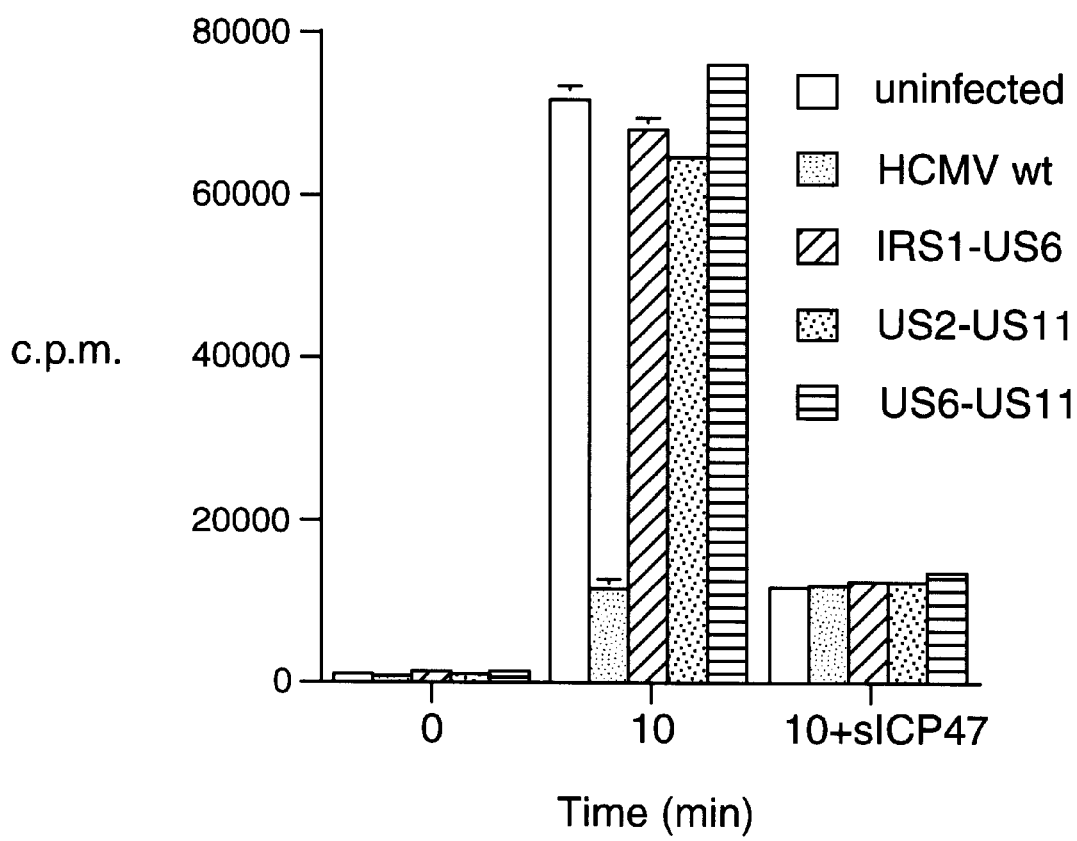
FIGS. 7A and 7B: US6 is responsible for TAP inhibition during HCMV infection Translocation of a reporter peptide library was measured in HFF cells infected with HCMV mutants containing deletions of multiple genes within the IRS1-US11 region (A) or with only US6 deleted (B). Peptide transport assays were performed as described in the material and methods section. As control, peptide recovery after 0 min incubation or after adding sICP47 was measured. HCMV mutants IRS1-US6, US2-US11, US6-US11 as well as US6 have been described previously (Jones et al., 1995).
Figure 7B:
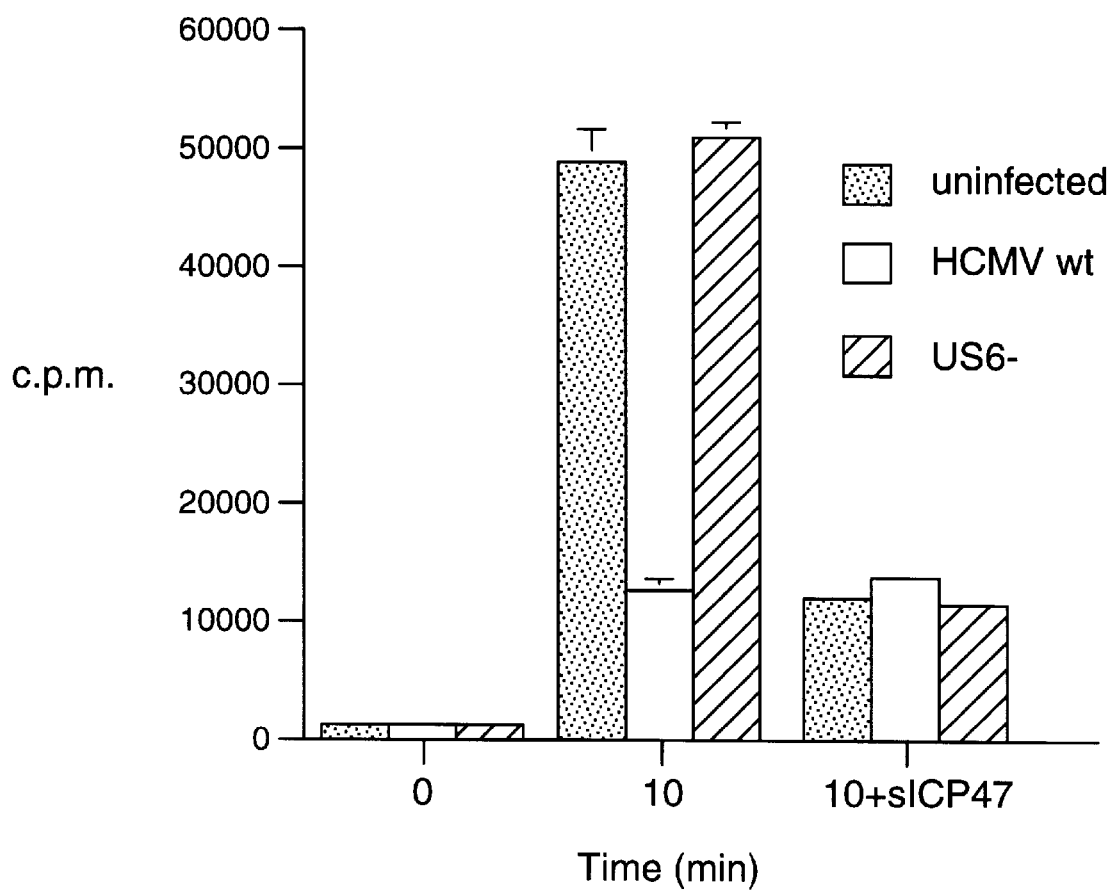

Recently, it was demonstrated that TAP transport is inhibited during HCMV infection (Hengel et al., 1996). Moreover, peptide translocation was restored upon deletion of a 15 kb fragment spanning US1-US15. To investigate whether US6 alone or in combination with other genes encoded in this region is responsible for TAP inhibition during HCMV infection, we analyzed peptide transport activity in cells infected with a series of HCMV mutants (Jones et al., 1995) containing the deletions IRS1-US6, US2-US11 and US6-US11 (FIG. 7A). HFF cells were infected either with HCMV wild type or with the deletion mutants for 72 hours at a m.o.i. of 5, and peptide translocation was measured by the recovery of glycosylated $^{125}$I-labeled reporter peptide library. In contrast to wildtype HCMV, none of these deletion mutants inhibited TAP-mediated peptide translocation in HFF infected cells, whereas peptide translocation was blocked when a synthetic version of ICP47 (sICP47) was added (FIG. 7A). Since the common gene absent from all these mutant viruses is US6, a deletion mutant lacking this gene was constructed. HFF cells were infected for 72 hours at a m.o.i of 5 with the mutant lacking the US6 gene. As shown in FIG. 4B, the absence of the US6 gene product restored TAP dependent peptide translocation in HFF cells. These results clearly demonstrate that US6 is solely responsible for the inhibition of peptide translocation in HCMV-infected cells.

Subcellular Localization of US6

Figure 8:
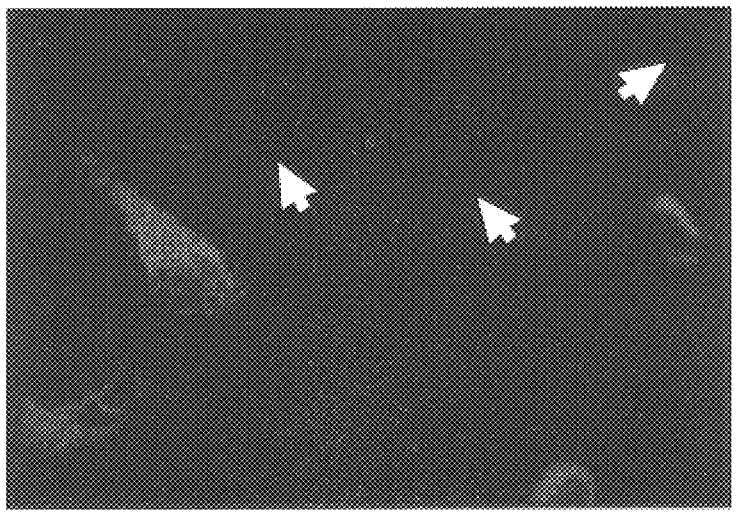
FIG. 8: Subcellular localization of US6 HtTa cells were transiently transfected with US6 and grown in the absence of tetracycline for 48 h. US6 was visualized using anti-US6N and goat-anti-rabbit-Rhodamin conjugate (Cappel). Calnexin was stained with AF8 (Sugita and Brenner, 1994) and visualized with goat-anti-mouse-FITC (Cappel). Non-transfected cells which express calnexin but not US6 are indicated by arrows. The same microscopic field was photographed at the excitation wavelengths of rhodamin (upper panel) fluorescein (lower panel), or both (middle panel).
Figure 8:
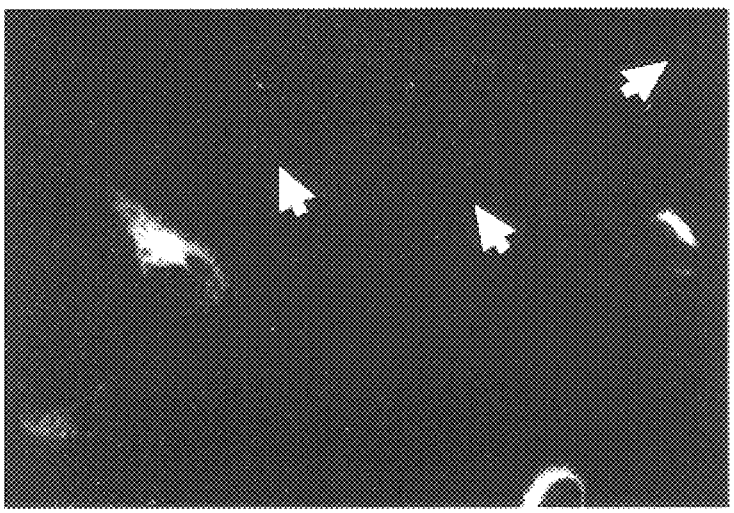
Figure 8:
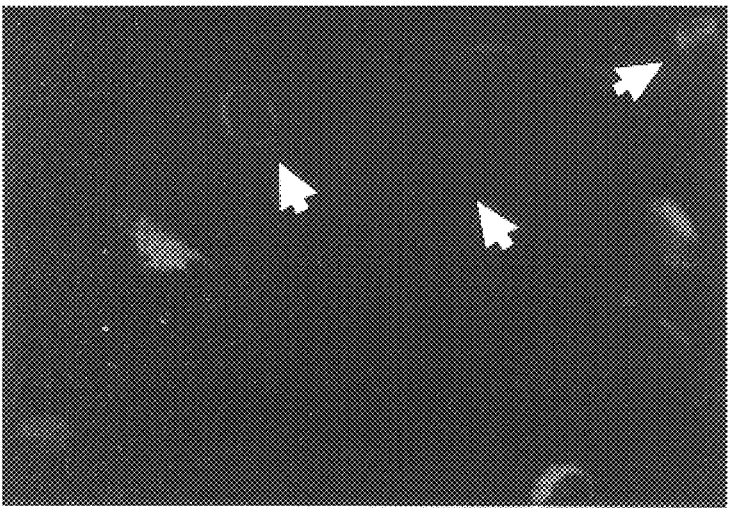

The observed functional similarity between ICP47 and US6 contrasts with their different predicted protein structure. ICP47 is a soluble protein containing 89 amino-acids which localizes to the cytosol (Früh et al., 1995; York et al., 1994), whereas the open reading frame US6 encodes a predicted type I transmembrane glycoprotein of 184 amino-acids with some degree of sequence homology to the ORFs US2-US11 (Ahn et al., 1996a; Chee et al., 1990). To study the subcellular localization of US6, we raised anti-peptide antibodies against the predicted luminal domain of US6 and compared by immunofluorescence analysis its intracellular localization with that of calnexin, an ER resident chaperone (Degen and Williams, 1991). When HeLa cells transiently transfected with US6 were probed with antiserum US6-N a perinuclear staining was observed for transfected cells but not for non-transfected cells (FIG. 8, arrows). A similar pattern was observed both for transfected and non-transfected cells with the calnexin-specific monoclonal antibody AF8 (FIG. 8, lower panel). Moreover, costaining indicated that both proteins localized to the same compartment (FIG. 8, middle panel). Thus, we conclude that US6 is an ER-resident glycoprotein as observed for US3 (Ahn et al., 1996a), US11 (Wiertz et al., 1996a) and a subpopulation of US2 (Wiertz et al., 1996b)

The ER Luminal Domain of US6 is Responsible for TAP Inhibition

Figure 9:
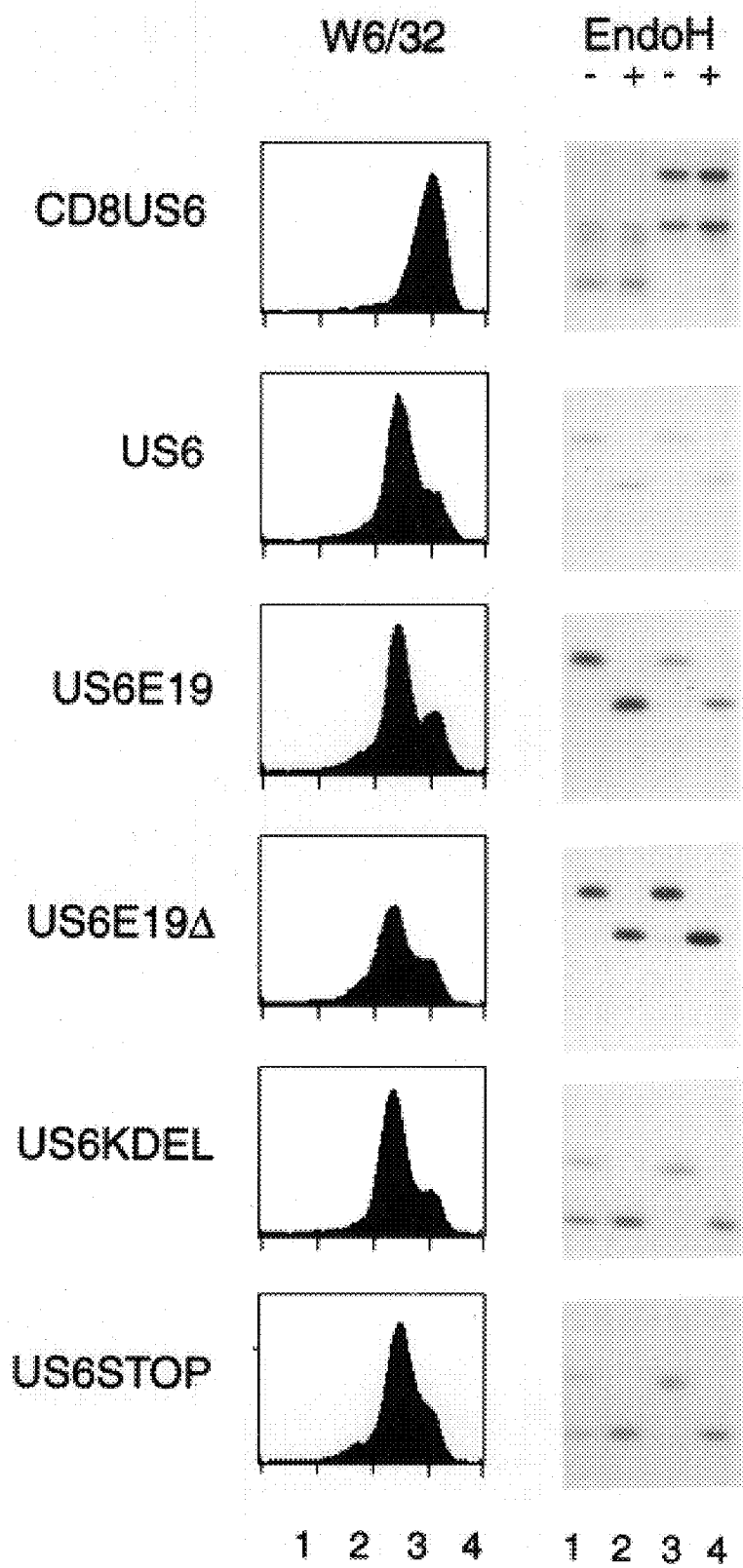
FIG. 9: The luminal domain of US6 is sufficient for ER-retention and MHC class I down-regulation is shown. HtTa cells were transiently transfected with the indicated constructs in the absence of tetracycline. 36 h after transfection, MHC class I surface expression was monitored by cytofluorometry using mab W6/32. Results are graphically depicted in the left panel as cell number versus mean fluorescence (log scale). The right panel shows the US6 derivatives immunoprecipitated with anti-US6N from NP40 lysates of transiently transfected HtTa cells labeled for 30 min (lane 1, 2) and chased for 4 h (lane 3, 4). Lanes 2 and 4 were treated with EndoH prior to SDS-PAGE. The right top panel was immunoprecipitated with anti-CD8 all other immunoprecipitations were carried out with anti-US6N. Intracellular transport of CD8 is indicated by the molecular weight shift due to addition of sialic acid. Since CD8 does not contain N-linked carbohydrates, it is not affected by EndoH. Compared to non-transfected HtTa cells, peptide transport activity was reduced between 50 to 63% in all transfectants except for CD8-US6 where no reduction was observed.

Since TAP inhibition by an ER resident protein has not been observed previously, we wanted to know if US6 inhibits TAP and/or is retained in the ER via its cytoplasmic, transmembrane or luminal domain. Therefore, we constructed a series of fusion proteins and examined their intracellular localization and transport as well as their ability to reduce MHC class I surface expression and peptide translocation (FIG. 9). When the cytoplasmic domain of CD8 was replaced with that of US6, surface levels of MHC class I remained unchanged (FIG. 9, CD8US6). Moreover, the cytoplasmic tail of US6 was unable to prevent the intracellular transport of CD8, in contrast to the cytoplasmnic tails of a number of ER resident proteins (Jackson et al., 1990). Thus it seems that the cytoplasmic tail of US6 is not sufficient for either ER retention or TAP inhibition. To examine whether the luminal domain of US6 alone would inhibit peptide transport we replaced both the predicted transmembrane domain and the cytoplasmic tail of US6 with that of CD8 and adenovirus E19, respectively. The resulting fusion protein US6E19 remained EndoH sensitive and downregulated MHC class I surface expression as a result of TAP-inhibition (FIG. 9). Interestingly, ER retention as well as TAP inhibition was also observed for the construct US6E19D which contains a deletion in the ER retention signal of the E19 tail (Jackson et al., 1990). These results suggested that the luminal domain of US6 is responsible for both ER retention and TAP inhibition. To examine whether the luminal domain needs to be anchored in the membrane in order to inhibit TAP we fused the luminal domain of US6 to the sequence KDEL, which retains soluble proteins in the ER. In addition, we truncated the US6 luminal domain by introducing a stop codon at amino acid position 139, i. e. before the predicted transmembrane domain. As shown in FIG. 9, both US6KDEL and US6STOP remained EndoH sensitive and both were able to prevent peptide translocation and thus class I surface expression. We conclude that the luminal domain of US6 is responsible for both inhibition of peptide translocation and ER retention of US6.

Association of US6 with the TAP/Class I Complex

Figure 10:
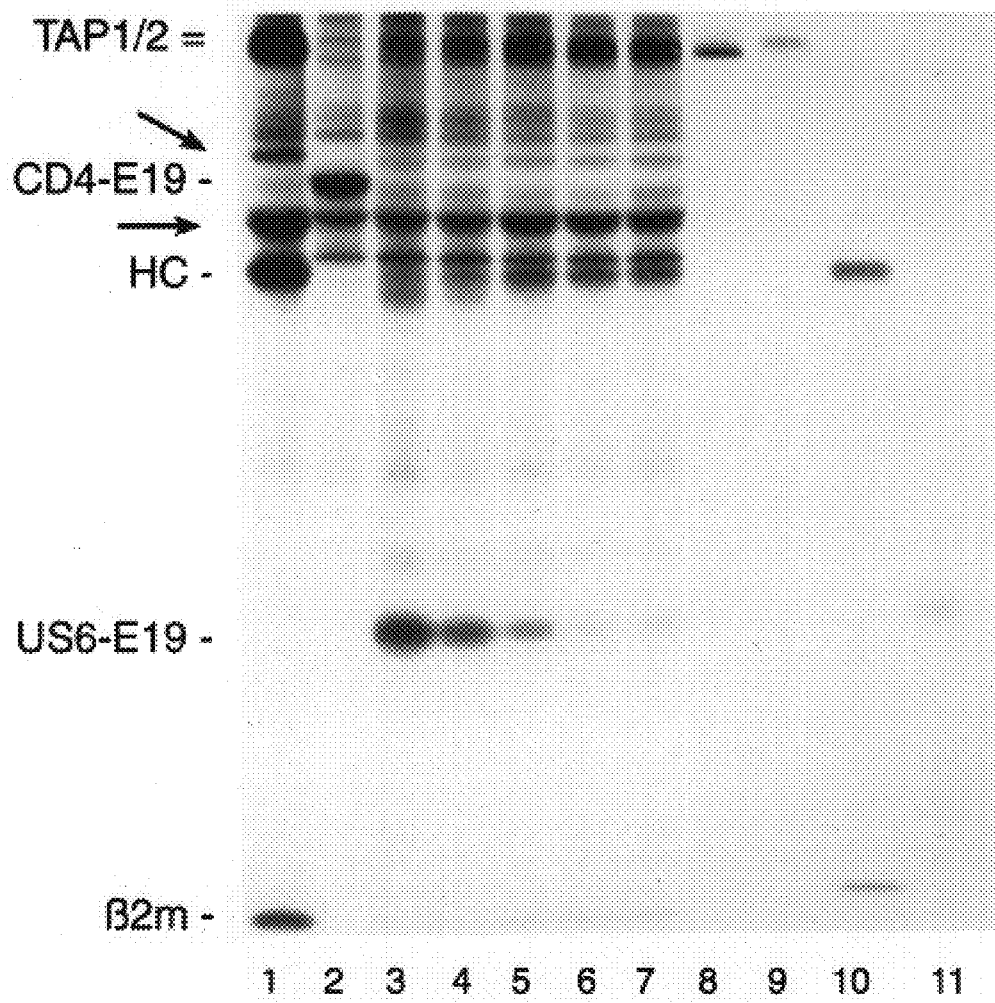
FIG. 10: The luminal domain of US6 interacts with TAP. HtTa cell were non-transfected (lane 1) or transfected with CD4E19.pCMUII (Jackson et al., 1990) (lane 2) or pUHG10.3-US6E19 (lane 3–7). Two days after transfection, cells were metabolically labeled for 16 h and proteins were solubilized in 1% digitonin and immunoprecipitated with anti-TAP1 (lane 1) or anti-E19 antiserum (Nilsson et al., 1989) (lane 2–7) and separated on SDS-PAGE (lanes 1–7). A fraction of the anti-E19 precipitate from US6-E19 transfected cells was dissolved in 1% SDS and reprecipitated with anti-TAP1 (lane 8), anti-TAP2 (lane 9), K455 (13) (anti-class I, (Andersson et al., 1985)) (lane 10) or anti-US6N (lane 11). (Lanes 1–7 and 8–11 are from different gels, hence the slightly different mobility of β2m). Prior to immunoprecipitation cells were grown for 24 h without tetracycline (lane 1–3) or with 0.0001, 0.001, 0.01, 0.1 µg/ml tetracycline (lanes 4–7) to achieve decreasing expression levels of US6E19. Proteins which are part of the TAP/class I complex as well as CD4E19 are indicated on the left. All other protein bands are non-specifically immunoprecipitated since they are present in all precipitations. Cells were treated for 24 h with interferon-g (1000 U/ml) prior to labeling to increase TAP expression.

It seemed likely that TAP inhibition and/or ER retention involved a direct interaction between US6 and TAP. However, neither of the two anti-US6 antisera co-immunoprecipitated TAP from lysates even when mild detergents were used for solubilization. This might be due to the possibility that these antisera are not able to recognize a US6/TAP complex because their epitopes are involved in TAP binding. Therefore, we used an antiserum against the E19 cytoplasmic tail to immunoprecipitate US6E19 from digitonin lysates of transiently transfected HeLa cells. We modulated the intracellular concentrations of both US6E19 and TAP by using tetracycline or Interferon-g, respectively. For control, we immunoprecipitated the TAP/class complex from HeLa cells using anti-TAP I antiserum which coprecipitates both MHC class I HC and b2m (FIG. 10, lane 1) and at least two additional proteins (arrows) with molecular weights corresponding to calreticulin (upper band) and tapasin (lower band) both of which are thought to be involved in class I binding to TAP (Sadasivan et al., 1996). Neither of these proteins was coprecipitated by anti-E19 from digitonin lysates of CD4E19 transfected cells (lane 2). By contrast, both TAP subunits as well as class I HC and b2m coprecipitated with US6E19 as shown by reprecipitation with the respective antibodies (FIG. 10, lanes 8–11). Also the two additional proteins were coprecipitated by anti-E19 indicating that US6 does not disrupt the TAP/class I complex. Interestingly, increasing amounts of TAP/class I complex were coprecipitated upon decreasing US6E19 expression levels (lane 3–7). We interpret this result as indication for a specific saturatable binding of US6, because upon saturation the ratio of free versus TAP-bound US6 increases with the intracellular concentration of US6. At high expression levels relatively more unbound US6 will be precipitated if limiting amounts of the E19-specific antiserum are used, as is the case in the experiment shown in FIG. 10. A very similar observation was made with ICP47, where the majority of ICP47 remains free in the cytosol upon overexpression whereas most ICP47 is bound to TAP at low concentrations (Früh et al., 1995). Since binding to TAP is saturatable it is unlikely that US6 is retained in the ER by binding to TAP, because US6E19 does not acquire EndoH resistance regardless of its expression levels (FIGS. 9, 10). However, the interaction of US6 with the TAP/class I complex might be required for blocking peptide translocation by TAP.

US6 does not Inhibit Peptide Binding to TAP

Figure 11:
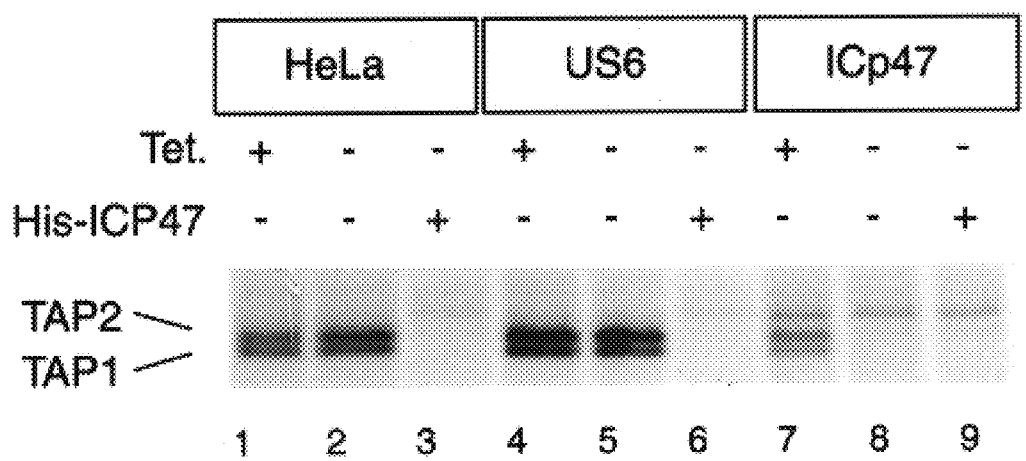
FIG. 11: Peptide binding to TAP in US6 transfected HeLa cells. Untransfected HtTa cells or HtTa cells stably transfected with US6 or ICP47 were grown in the presence or absence of tetracycline prior to SLO permeabilization and incubation with photoreactive peptide together with 1 µM purified recombinant His-ICP47 as described (Ahn et al., 1996b). After UV-crosslinking, heterodimeric TAP molecules were precipitated with anti-TAP1 antiserum and separated on SDS-PAGE. The relative position of TAP1 and TAP2 is indicated.

The association of US6 with the luminal portion of TAP is in contrast to ICP47 which approaches TAP from the cytosol. These different modes of interaction might be reflected in different molecular mechanisms of TAP inhibition. We demonstrated previously that ICP47 does not inhibit ATP-binding to TAP but competes with peptides for binding to the substrate binding site of TAP (Ahn et al., 1996b). Likewise we did not observe an inhibition of ATP binding to TAP from US6 expressing cells. To test whether US6 would interfere with peptide binding we added labeled peptides carrying a photocrosslinker to SLO permeabilized cells expressing US6 (FIG. 11). As control we used ICP47-transfected and non-transfected HeLa cells. In agreement with our previous observations (Ahn et al., 1996b), peptides could not be crosslinked to TAP isolated from ICP47-expressing cells (FIG. 11, lane 8) or from HeLa cells treated with purified recombinant His-ICP47 (FIG. 11, lane 3). By contrast, US6 expression did not prevent peptide binding (lane 5). Moreover, ICP47-binding to TAP was not affected by US6, since His-ICP47 inhibited peptide binding in US6-expressing cells (lane 6). We conclude that US6 interacts with a different domain of TAP compared to ICP47 and that US6 inhibits TAP by a different mechanism.

Our study shows that HCMV prevents MHC class I antigen presentation by the concerted effort of several proteins encoded in the US region. Four proteins, US2, US3, US6 and US11 specifically affect the intracellular transport of MHC class I molecules but not of other glycoproteins. The USII-mediated heavy chain degradation has been described previously (Jones, T. R. et al., (1995), J. Virol., 69, 4830–4841; Wiertz, E. J. et al., (1996) Cell, 84, 769–779). Furthermore, from our results it can be deduced that US2 works similar to US11, since a HCMV deletion mutant which only contains US2, US3, US4 and US5 is able to degrade heavy chains (Jones, T. R. et al., (1995) supra) and our results rule out US3, US4 and US5. The fate of the MHC class I molecules differs from US11 transfected cell lines with US3 retaining fully assembled MHC class I heterotrimers, whereas US6 expression prevents heterodimer formation.

HCMV infection causes major health problems in immunosuppressed individuals. Such infections result either from a relapse of a latent infections or they are caused by virus present in the transplanted tissue. To clear HCMV from either the donor or the recipient or both prior to transplantation it would be useful to induce an immune response against the virus. Expression of the US proteins most likely prevents the immune system to detect ongoing infections. This immune escape could potentially be reverted by developing compounds which prevent the interaction of US proteins with MHC class I molecules. Thus, US proteins are potential drug targets. Our results identify US3 and US6 as potential targets, in addition to US2 and US11. Since US3 might be expressed during the latent phase, it could be a more important target to activate an immune response against the latent stage of the virus.

For gene therapy, viral vectors which express the gene of interest are introduced into the patient or experimental animal. The major goal of this process is to achieve long-term stable expression of the introduced healthy gene. However, a major obstacle to gene therapy is the rapid loss of recombinant gene expression which is associated with the development of a vigorous inflammatory response. For E1-deleted adenovirus vectors, inflammation is initiated by vector-specific CTL as shown by passive transfer experiments and depends on MHC class I presentation since transduced cells were not eliminated in β2m -/- mice (Yang, Y., Ertl, C. J. & Wilson, J. M. (1994) *Iinmuizit-* 1, 433–442). Thus, it seems possible that by introducing viral proteins which prevent MHC class I presentation such unwanted inflammatory responses could be prevented. Indeed, the constitutive expression of E19 reduced the vector-specific CTL response (Lee, M. G., Abina, M. A., Haddada, H. & Perricaudet, M. (1995) *Gene Ther.* 2, 256–61). Introducing ICP47 as well as US proteins into such vectors might further reduce such a CTL response, since MHC class I antigen presentation will be inhibited on several levels. The viral proteins described here could be useful in additional situations where CTL reactivity is unwanted. M. Horwitz and coworkers have recently demonstrated that transgenic expression of the adenovirus E3 region, which contains E19 acting similar to US3, in pancreatic islet cells prolonged the survival of islets transplanted across haplotype barriers (Horwitz, M. S., Tufariello, J., Grunhaus, A. & Fejer, G. (1995) *Curr Top Microbiol Immuizol* 199, 195–211). Thus, the proteins described here might be useful in transplantation, e. g. xenotransplantation from transgenic-animals.

Finally, US6 is useful to induce peptide specific CTL in vitro, similar to TAP-deleted cell lines (De Bruijn, M. L., Schumacher, T. N., Nieland, J. D., Ploegh, H. L., Kast, W. M. & Mellef, C. J. (1991) *Eur J Immunol* 21, 2963–70). It might be possible to bind β2m to the free MHC class I molecules which reach the cell surface in US6-transfected cells. Similar to cells lacking functional TAP such molecules should be very efficiently loaded with synthetic peptides specific for the respective MHC class I haplotype. Such mono-specific antigen presenting cells are excellent stimulators to induce peptide-specific primary CTL in vitro (De Bruijn, M. L., Schumacher, T. N., Nieland, J. D., Ploegh, H. L., Kast, W. M. & Mellef, C. J. (1991) *Eur J Iinmuiiol* 21, 2963–70). This should facilitate the generation of cytotoxic T cells specific for a given antigen, a prerequisite for T cell based vaccines against cancer or viral infections.

References

Ahn, K., Angulo, A., Ghazal, P., Peterson, P. A., Yang, Y., and Früh, K. (1996a). Human cytomegalovirus inhibits antigen presentation by a sequential multitep process. Proc. Natl. Acad. Sci. USA 93, 10990–10995.

Ahn, K., Meyer, T. H., Uebel, S., Sempé, P., Djaballah, H., Yang, Y., Peterson, P. A., Früh, K., and Tampé, R. (1996b). Molecular mechanism and species specificity of TAP inhibition by Herpes simplex virus protein ICP47. EMBO J. 15, 3247–3255.

Andersson, M., Pääbo, S., Nilsson, T., and Peterson, P. A. (1985). Impaired intracellular transport of class I MHC antigens as a possible means for adenoviruses to evade immune surveillance. Cell 43, 215–222.

Androlewicz, M. J., and Cresswell, P. (1994). Human Transporters associated with antigen processing possess a promiscuous peptide-binding site. Immunity 1, 7–14.

Androlewicz, M. J., Ortmann, B., Van Endert, P. M., Spies, T., and Cresswell, P. (1994). Characteristics of peptide and major histocompatibility complex class I/beta2-microglobulin binding to the transporters associated with antigen processing (TAP1 and TAP2). Proc Natl Acad Sci USA 91, 12716–12720.

Burgert, H.-G., and Kvist, S. (1985). An adenovirus type 2 glycoprotein blocks cell surface expression of human histocompatibility class I antigens. Cell 41, 987–997.

Chee, M. S., Bankier, A. T., Beck, S., Bohni, R., Brown, C. M., Cerny, R., Horsnell, T., Hutchinson III, C. A., Kouzarides, T., Martignetti, J. A., Preddie, E., Satchwell, S. C., Tomlinson, P., Weston, K. M., and Barrell, B. G. (1990). Analysis of the protein-coding content of the sequence of human cytomegalovirus strain AD169. Curr. Top. Microbiol. Immunol. 154, 125–169.

Degen, E., and Williams, D. B. (1991). Participation of a novel 88-kD protein in the biogenesis of murine class I histocompatibility molecules. J. Cell. Biol. 112, 1099–1115.

Fleckenstein, B., Muller, I., and Collins, J. (1982). Cloning of the complete human cytomegalovirus genome in cosmids. Gene 18, 39–46.

Früh, K., Ahn, K., Djaballah, H., Sempé, P., van Endert, P. M., Tampé, R., Peterson, P. A., and Yang, Y. (1995). A viral inhibitor of peptide transporters for antigen presentation. Nature 375, 415–418.

Früh, K., Ahn, K., and Peterson, P. A. (1997). Inhibition of MHC class I antigen presentation by viral proteins. J. Mol. Med. 75, 18–27.

Gilbert, M. J., Riddel, S. R., Plachter, B., and Greenberg, P. D. (1996). Cytomegalovirus selectivity blocks antigen processing and presentation of its immediate-early gene product. Nature (London) 383, 720–722.

Gossen, M., and Bujard, H. (1992). Tight control of gene expression in mammalian cells by tetracycline-responsive promoters. Proc. Natl. Acad. USA 89, 5547–5551.

Hammond, C., and Helenius, A. (1994). Quality control in the secretory pathway: retention of a misfolded viral membrane glycoprotein involves cycling between the ER, intermediate compartment, and Golgi apparatus. J. Cell Biol. 126, 41–52.

Heemels, M. T., Schumacher, T. N., Wonigeit, K., and Ploegh, H. L. (1993). Peptide translocation by variants of the transporter associated with antigen processing. Science 262, 2059–63.

Henderson, R. A., Michel, H., Sakaguchi, K., Shabanowitz, J., Appella, E., Hunt, D. F., and Engelhard, V. H. (1992). HLA-A2.1-associated peptides from a mutant cell line: a second pathway of antigen presentation. Science 255, 1264–6.

Hengel, H., Flohr, T., Haemmerling, G. J., Koszinowski, U. H., and Momburg, F. (1996). Human cytomegalovirus inhibits peptide translocation into the endoplasmic reticulum for MHC class I assembly. J. Gen. Virol. 77, 2287–2296.

Hill, A., Jugovic, P., York, I., Rus, G., Bennink, J., Yewdell, J., Ploegh, H., and Johnson, D. (1995). Herpes simplex virus turns off the TAP to evade host immunity. Nature 375, 411–415.

Jackson, M. R., Nilsson, T., and Peterson, P. A. (1990). Identification of a consensus motif for retention of transmembrane proteins in the endoplasmic reticulum. EMBO J 9, 3153–62.

Jones, R. T., Wiertz, E. J. H. J., Sun, L., Fish, K. N., Nelson, J. A., and Ploegh, H. (1996). Human cytomegalovirus US3 impairs transport and maturation of major histocompatibility complex calss I heavy chains. Proc. Natl. Acad. Sci. USA 93, 11327–11333.

Jones, T. R., Hanson, L. K., Sun, L., Slater, J. S., Stenberg, R. M., and Campbell, A. E. (1995). Multiple independent loci within the human cytomegalovirus unique short region down-regulate expression of major histocompatibility complex class I heavy chains. Journal of Virology 69, 4830–41.

Jones, T. R., and Muzithras, V. P. (1991). Fine mapping of transcripts expressed from the US6 gene family of human cytomegalovirus strain AD169. Journal of Virology 65, 2024–36.

Kelly, A., Powis, S. H., Kerr, L.-A., Mockridge, I., Elliott, T., Bastin, J., Uchanska-Ziegler, B., Ziegler, A., Trowsdale, J., and Townsend, A. (1992). Assembly and function of the two ABC transporter proteins encoded in the human major histocompatibility complex. Nature 355, 641–44.

Kozak, M. (1984). Compilation and analysis of sequences upstream from the translational start site in eukaryotic mRNAs. Nucleic Acid Res. 12, 857–872.

Lehner, P. J., and Cresswell, P. (1996). Processing and delivery of peptides presented by MHC class I molecules. Curr. Op. Immunol. 8, 59–67.

Levitskaya, J., Coram, M., Levitsky, V., Imreh, S., Steigerwald-Mullen, P. M., KLein, G., Kurilla, M. G., and Masucci, M. G. (1995). Inhibition of antigen processing by the integral repeat region of the Ebstein-Barr virus nuclear antigen-1. Nature 375, 685–688.

Müller, K. M., Ebensperger, K. M., and Tampé, R. (1994). Nucleotide binding to the hydrophilic C-terminal domain of the transporter associated with antigen-processing (TAP). J. Biol. Chem. 269, 14032–14037.

Neefjes, J. J., Momburg, F., and Hämmerling, G. J. (1993). Selective and ATP-dependent translocation of peptides by the MHC-encoded transporter. Science 261, 769–771.

Nijenhuis, M., and Hämmerling, G. J. (1996a). Multiple regions of the transporter associated with antigen processing (TAP) contribute to its peptide binding site. J. Immunol. 157, 5467–5477.

Nijenhuis, M., Schmitt, S., Armandola, E. A., Obst, R., Brunner, J., and Hämmerling, G. J. (1996b). Identification of a contact region for peptide on the TAP1 chain of the transporter associated with antigen processing. J Immunol 156, 2186–2195.

Nilsson, T., Jackson, M., and Peterson, P. A. (1989). Short cytoplasmic sequences serve as retention signals for transmembrane proteins in the endoplasmic reticulum. Cell 58, 707–18.

Parham, P. (1983). Monoclonal antibodies against HLA products and their use in immunoaffinity purification. Meth. Enzymol. 92, 110–138.

Sadasivan, B., Lehner, P. J., Ortmann, B., Spies, T., and Cresswell, P. (1996). Roles for calreticulin and a novel glycoprotein, tapasin, in the interaction of MHC class I molecules with TAP. Immunity 5, 103–114.

Shepherd, J. C., Schumacher, T. N. M., Ashton-Rickardt, P. G., Imaeda, S., Ploegh, H., Janeway, C. A., and Tonegawa, S. (1993). TAP1-dependent peptide translocation in vitro is ATP-dependent and selective. Cell 74, 577–584.

Sugita, M., and Brenner, M. B. (1994). An unstable beta 2-microglobulin: major histocompatibility complex class I heavy chain intermediate dissociates from calnexin and then is stabilized by binding peptide. J. Exp. Med/ 180, 2163–2171.

Tomazin, R., Hill, A. B., Jugovic, P., York, I., van Endert, P., Ploegh, H. L., Andrews, D. W., and Johnson, D. (1996). Stable binding of the herpes simplex virus ICP47 protein to the peptide binding site of TAP. EMBO J. 15, 3256–3266.

Townsend, A., and Bodmer, H. (1989). Antigen recognition by class I-restricted T lymphocytes. Ann. Rev. Immunol. 7, 601–624.

Townsend, A., Elliot, T., Cerundolo, V., Foster, L., Barber, B., and Tse, A. (1990). Assembly of class I molecules analysed in vitro. Cell 62, 285.

Trowsdale, J., Hanson, I., Mockridge, I., Beck, S., Townsend, A., and Kelly, A. (1990). Sequences encoded in the class II region of the MHC related to the 'ABC' superfamily of transporters. Nature 348, 741–44.

Van Endert, P. M., Tampé, R., Meyer, T. H., Tisch, R., Bach, J.-F., and McDevitt, H. O. (1994). A sequential model for peptide binding and transport by the transporters associated with antigen processing. Immunity 1, 491–500.

Wang, K., Früh, K., Peterson, P. A., and Yang, Y. (1994). Nucleotide binding of the C-terminal domains of the major histocompatibili ty complex-encoded transporter expressed in Drosophila melanogaster cells. Febs Lett 350, 337–341.

Wei, M. L., and Cresswell, P. (1992). HLA-A2 molecules in an antigen-processing mutant cell contain signal sequence-derived peptides. Nature 356, 443–6.

Wiertz, E. J. H. J., Jones, T. R., Sun, L., Bogyo, M., Geuze, H. J., and Ploegh, H. L. (1996a). The human cytomegalovirus US11 gene product dislocates MHC class I heavy chains from the ER to the cytosol. Cell 84, 769–779.

Wiertz, E. J. H. J., Tortorella, D., Bogyo, M., Yu, J., Mothes, W., Jones, T. R., Rapoport, T. A., and Ploegh, H. L. (1996b). Sec61-mediated transfer of a membrane protein from the endoplasmic reticulum to the proteasome for destruction. Nature 384, 432–438.

Yang, Y., Früh, K., Ahn, K., and Peterson, P. A. (1995). In vivo assembly of the proteasomal complexes, implications for antigen processing. J. Biol. Chem. 270, 27687–27694.

Yang, Y., Waters, J. B., Früh, K., and Peterson, P. A. (1992). Proteasomes are regulated by interferon gamma: implications for antigen processing. Proc Natl Acad Sci USA 89, 4928–32.

York, I. A., Roop, C., Andrews, D. W., Riddell, S. R., Graham, F. L., and Johnson, D. C. (1994). A cytosolic Herpes simplex protein inhibits antigen presentation to CD8+ T lymphocytes. Cell 77, 525–535.

What is claimed is:

1. A recombinant human cytomegalovirus (HCMV) mutant comprising a genome from which a gene sequence capable of down-regulating major histocompatibility complex (MHC) class I expression has been deleted, wherein the deleted gene sequence is in open reading frame US3 and entire open reading frame of US6 only.

2. A method of down-regulating major histoconmpatibility complex (MHC) class I expression in a cell comprising transferring an expression vector containing HCMV open reading frame US3 and US6 only into a cell.

3. A pharmaceutical composition comprising a recombinant human cytomegalovirus (HCMV) mutant which comprises a genome from which a gene sequence capable of down-regulating, major histocompatibility complex (MHC) class I expression has been deleted, wherein the deleted gene sequence is in open reading frame US3 and/or US6 only, and a pharmaceutically acceptable carrier.

4. The pharmaceutical composition of claim 3 for use in the prevention or treatment of cytomegalovirus infections, wherein the deleted gene sequence is in open reading frame US3 and/or entire open reading frame US6.

5. The pharmaceutical composition of claim 4, further comprising an adjuvant.

* * * * *